United States Patent
Sato et al.

(10) Patent No.: US 7,157,539 B2
(45) Date of Patent: Jan. 2, 2007

(54) POLYMERIZABLE COMPOUND, POLYMER COMPOUND AND BLOCK POLYMER COMPOUND, AND COMPOSITION, IMAGE-FORMING METHOD AND IMAGE-FORMING APPARATUS USING THE SAME

(75) Inventors: Koichi Sato, Kanagawa (JP); Ikuo Nakazawa, Kanagawa (JP); Sakae Suda, Kanagawa (JP); Masayuki Ikegami, Kanagawa (JP); Keiichiro Tsubaki, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 356 days.

(21) Appl. No.: 10/422,537

(22) Filed: Apr. 24, 2003

(65) Prior Publication Data

US 2003/0236343 A1 Dec. 25, 2003

(30) Foreign Application Priority Data

| Apr. 26, 2002 | (JP) | ............................. 2002-126159 |
| Jul. 3, 2002 | (JP) | ............................. 2002-195117 |
| Oct. 1, 2002 | (JP) | ............................. 2002-289167 |
| Apr. 3, 2003 | (JP) | ............................. 2003-100164 |

(51) Int. Cl.
*C08F 212/00* (2006.01)
*C08F 216/12* (2006.01)

(52) U.S. Cl. ....................................... 526/334; 526/333
(58) Field of Classification Search ................ 524/505, 524/612; 523/160, 161; 526/320, 326, 333, 526/334
See application file for complete search history.

(56) References Cited

U.S. PATENT DOCUMENTS

| 4,313,124 A | 1/1982 | Hara et al. |
| 4,345,262 A | 8/1982 | Shirato et al. |
| 4,459,600 A | 6/1984 | Sato et al. |
| 4,463,359 A | 7/1984 | Ayata et al. |
| 4,558,333 A | 12/1985 | Sugitani et al. |
| 4,723,129 A | 2/1988 | Endo et al. |
| 4,740,796 A | 4/1988 | Endo et al. |
| 5,198,319 A | 3/1993 | Kato |
| 5,399,631 A * | 3/1995 | Egawa et al. ............. 525/328.9 |
| 6,033,466 A * | 3/2000 | Ito .............................. 106/486 |
| 6,391,923 B1 * | 5/2002 | Pollmann et al. ........... 514/714 |
| 6,616,946 B1 * | 9/2003 | Meier et al. ................ 424/489 |
| 2003/0050364 A1* | 3/2003 | Sato et al. ................... 523/160 |
| 2003/0153649 A1* | 8/2003 | Bromberg ................... 523/160 |

FOREIGN PATENT DOCUMENTS

| EP | 1243624 A1 | 9/2002 |
| EP | 1285948 A2 | 2/2003 |
| EP | 1 422 255 | 5/2004 |
| JP | 59-12670 | 7/1984 |
| JP | 59-138461 | 8/1984 |
| JP | 11-80221 | 3/1999 |
| JP | 11-322866 | 11/1999 |
| JP | 11-322942 | 11/1999 |
| WO | 02/100918 | 12/2002 |
| WO | WO-02/100918 A1 | 12/2002 |

OTHER PUBLICATIONS

Laus, Michele, Bignozzi, Maria Chiara, Fagnani, Marco, and Angeloni, Annino Sante; "Liquid Crystalline Poly(vinyl ether)s and Block Copoly(vinyl ether)s by Living Cationic Polymerization", Macromolecules, vol. 29(15), 1996 (pp. 5111-5118).*
Morrison, Robert Thornton and Boyd, Robert Neilson; Organic Chemistry 5th Edition, Allyn and Bacon, Inc. Boston, 1987 (p. 700).*
Takeuchi, et al. "Living Cationic Polymerization of Ethyl 2-(Vinyloxy) Ethoxyacetate: A Vinyl Ether with an Ether and an Ester function in the pendant" Journal of Polymer Science, Polymer Chemistry Edition, John Wiley and Sons. New York, US, vol. 27, No. 10, Sep. 1, 1989 pp. 3303-3314.
Rahman, et al. Cataionic Polymerization of Vinyl Ether with a Benzoate Pendant: The formation of long-lived polymers and the identification of side reactions J Polymer Science Part A; A Journal of Polymer Science, Part A: Polymer Chemistry Dec. 2000 John Wiley & Sons Inc. New York, NY US vol. 38, No. 24, Dec. 2000 pp. 4362-4372.
Hashimoto, et al. "Cationic Polymerization of Vinyl Ethers with a Benzoate or Phenylacetate Pendant: Synthesis of New Poly (Carboxylic Acid)s with Poly (Vinyl Ether) Backbone" Journal of Macromolecular Science Pure and Applied Chemistry, A 36(3), pp. 449-460 (1999).
European Examination Report for EP 03 009 325.6 dated Apr. 5, 2006.

* cited by examiner

*Primary Examiner*—Callie Shosho
(74) *Attorney, Agent, or Firm*—Morgan & Finnegan, LLP

(57) ABSTRACT

A composition containing a polymer compound and medium being a solvent or a binder resin, wherein the polymer compound comprises monomer units represented by the general formula (1):

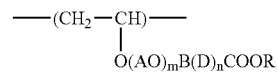

wherein A is a straight-chain or branched alkylene group of 1 to 15 carbon atoms, which may be substituted; m is an integer of 0 to 30, and; B is a single bond or alkylene, which may be substituted; D is an aromatic ring structure; n is an integer of 1 to 10, and R is a hydrogen atom, an alkyl group, which may be substituted, an aromatic ring structure, or a mono- or poly-valent metal cation.

4 Claims, 1 Drawing Sheet

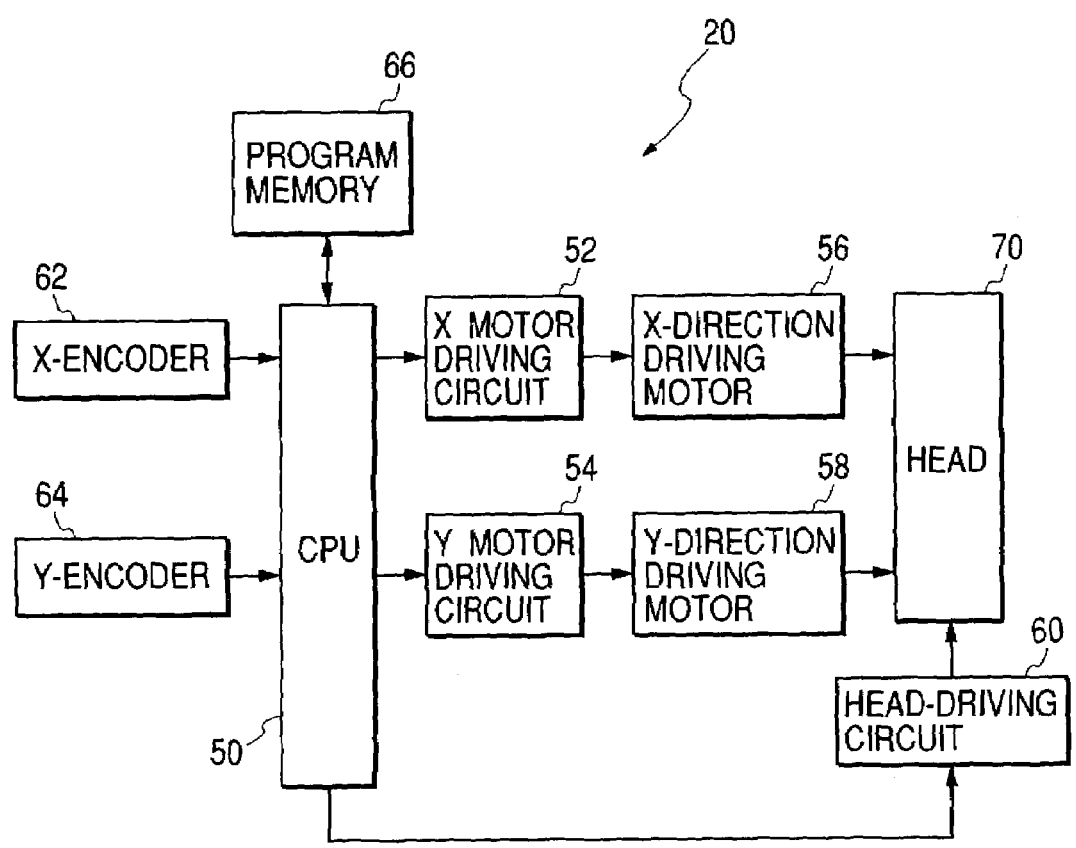

POLYMERIZABLE COMPOUND, POLYMER COMPOUND AND BLOCK POLYMER COMPOUND, AND COMPOSITION, IMAGE-FORMING METHOD AND IMAGE-FORMING APPARATUS USING THE SAME

BACKGROUND OF THE INVENTION

1. Field of the Invention

The present invention relates to novel polymerizable compounds, polymer compounds and block polymer compounds useful as various functional materials. The present invention also relates to compositions using the same, as well as image-forming methods and image-forming apparatuses using the same. Specifically, the present invention relates to recording materials using the above compound with a solvent or dispersion medium, ink compositions or toner compositions using the above compound with a colorant, as well as various image-forming methods and apparatuses using such compositions.

2. Related Background Art

Various ink or toner compositions have been prepared dissolving or dispersing a colorant in a medium, and for this purpose, various polymer compounds have been preferably used such as styryl, acrylic and methacrylic polymers. In production of solvent- or water-based colorant compositions, improvement of dispersibility of the colorant, e.g., pigment, has been tried using a polymer compound preferably those having an ionic functional group.

Meanwhile, polymer compounds having a polyvinyl ether main chain are known to be polymer materials having a flexible polymer chain. Heretofore, however, few attempts have been made to incorporate an ionic functional group to the monomer unit of a polymer compound. Only the following documents 1 and 2 describe several carboxylic acids and esters thereof as potential compounds for this purpose. At present, more stability is required for such a compound, as well as higher dispersibility and stability in a composition.

1. Journal of Polymer Science, Part A, Polymer chemistry, vol.27, pp. 3303 to 3314 (1989)
2. Pure Applied Chemistry, Vol.A36, No.3, pp. 449 to 460 (1999)

SUMMARY OF THE INVENTION

The present invention was made in consideration of the above conditions. The inventors of the present invention made this invention after the extensive study of the conventional techniques and problems involved therein.

The following patent documents 1 to 12 are incorporated herein for describing the present invention:

1. U.S. Pat. No. 4,723,129
2. U.S. Pat. No. 4,740,796
3. U.S. Pat. No. 4,463,359
4. U.S. Pat. No. 4,345,262
5. U.S. Pat. No. 4,313,124
6. U.S. Pat. No. 4,558,333
7. U.S. Pat. No. 4,459,600
8. Japanese Patent Application Laid-Open No. 59-123670
9. Japanese Patent Application Laid-Open No. 59-138461
10. Japanese Patent Application Laid-Open No. 11-080221
11. Japanese Patent Application Laid-Open No. 11-322942
12. Japanese Patent Application Laid-Open No. 11-322866.

One object of the present invention is to provide a polymer compound and a block polymer compound suitable for achieving good dispersibility of a colorant or a solid for ink and toner compositions.

Another object of the present invention is to provide a stable, novel polymerizable compound to produce the above polymer compound.

Still another object of the present invention is to provide an image-forming method and image forming apparatus that use a recording material such as ink and toner composition containing the above polymer compound.

According to the first aspect of the present invention, there is provided a composition that comprises a polymer compound and a medium being a solvent or a binder resin, the polymer compound comprising a monomer unit represented by the general formula (1):

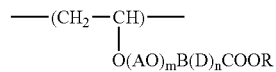

wherein A is a straight-chain or branched alkylene group of 1 to 15 carbon atoms with or without substitution; m is an integer of 0 to 30, and when m is 2 or more, A is the same or different each other; B is a single bond or an alkylene with or without substitution; D is an aromatic ring structure; n is an integer of 1 to 10, and when n is 2 or more, D is the same or different with each other; and R is a hydrogen atom, an alkyl group with or without substitution, or an aromatic ring structure with or without substitution.

According to the second aspect of the present invention, there is provided a composition comprising a medium being a solvent or a binder resin, and a monomer unit represented by the general formula (2)

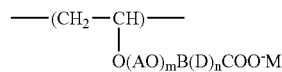

wherein A is a straight-chain or branched alkylene group of 1 to 15 carbon atoms with or without substitution; m is an integer of 0 to 30, and when m is 2 or more, A is the same or different from each other; B is a single bond or alkylene with or without substitution; D is an aromatic ring structure; n is an integer of 1 to 10, and when n is 2 or more, D is the same or different from each other; and M is a mono- or poly-valent metal cation.

The polymer compound comprising monomer units represented by the general formula (1) or (2) is preferably a block polymer compound, and the block polymer compound having a block structure of monomer units represented by the general formula (1) or (2) is preferably amphipathic.

In relation to the first and second aspects, there is provided a composition comprising a block polymer compound and a solvent or a binder resin, wherein the block polymer compound has a main chain of polyvinyl ether and comprises monomer units of an organic acid of which pKa is 4.50 or less or a salt thereof.

In relation to the first and second aspects, there is provided a composition comprising a block polymer, a solvent or binder resin and a colorant, wherein the block polymer comprises at least one monomer unit selected from the group consisting of carboxylic acid ester, carboxylic acid and carboxylic acid salt.

The third aspect of the present invention is a recording material comprising a composition described above.

According to the present invention, the recording material is a toner composition comprising a binder resin, a colorant, and a polymer compound or block polymer compound comprising monomer units represented by the general formula (1) or (2); or an ink composition comprising a solvent, a colorant, and a polymer compound or block polymer compound comprising monomer units represented by the general formula (1) or (2).

In relation to the third aspect of the present invention, there is provided a recording method comprising a step of thickening the above composition by contacting the composition to hydrogen ions or metal cations.

The present invention also provides an image-forming method characterized in that the above ink composition is deposited by ink-jet recording on a recording medium.

According to the fourth aspect of the present invention, there is provided a polymerizable compound represented by the general formula (3):

$$CH_2=CHO(AO)_mB(D)_nCOOR$$

wherein A is a straight-chain or branched alkylene group of 1 to 15 carbon atoms with or without substitution; m is an integer of 0 to 30, and when m is 2 or more, A is the same or different from each other; B is a single bond or alkylene with or without substitution; D is an aromatic ring structure; n is an integer of 2 to 10, and D is the same or different from each other; and R is a hydrogen atom, an alkyl group with or without substitution, or an aromatic ring structure with or without substitution.

According to the fifth aspect of the present invention, there is provided a polymer compound comprising a monomer unit represented by the general formula (4):

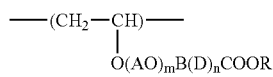

wherein A is a straight-chain or branched alkylene group of 1 to 15 carbon atoms with or without substitution; m is an integer of 0 to 30, and when m is 2 or more, A is the same or different from each other; B is a single bond or alkylene with or without substitution; D is an aromatic ring structure; n is an integer of 2 to 10, and D is the same or different from each other; and R is a hydrogen atom, an alkyl group with or without substitution, or an aromatic ring structure with or without substitution.

According to the sixth aspect of the present invention, there is provided a polymer compound comprising monomer units represented by the general formula (5):

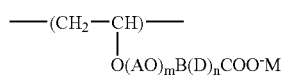

General Formula (5)

wherein A is a straight-chain or branched alkylene group of 1 to 15 carbon atoms with or without substitution; m is an integer of 0 to 30, and when m is 2 or more, A is the same or different from each other; B is a single bond or alkylene with or without substitution; D is an aromatic ring structure; n is an integer of 2 to 10, and D is the same or different from each other; and M is a mono- or poly-valent metal cation.

According to the seventh aspect of the present invention, there is provided a block polymer compound comprising monomer units represented by the general formula (1).

According to the eighth aspect of the present invention, there is provided a block polymer compound comprising monomer units represented by the general formula (2).

The block polymer compound comprising monomer units represented by the general formula (1) or (2) is preferably amphipathic.

According to the ninth aspect of the present invention, there is provided a block polymer compound having a main chain of polyvinyl ether and comprising organic acid monomer units having pKa of 4.50 or less or salt thereof. The present invention provides a block polymer compound of polyvinyl ether structure, wherein at least one type of monomer unit selected from the group consisting of a carboxylic acid ester, carboxylic acid or carboxyl acid salt is present in the monomer units. Block polymer of the present invention is also called block copolymer.

BRIEF DESCRIPTION OF THE DRAWING

FIGURE is a block diagram illustrating a structure of an ink-jet recording apparatus.

DESCRIPTION OF THE PREFERRED EMBODIMENTS

The present invention will be described in detail below.

<Polymer Compound Contained in the First Aspect of the Present Invention>

The polymer compound to be contained in the composition of the first aspect of the present invention, comprising monomer units represented by the general formula (1), is described in detail.

More specifically, the monomer unit represented by the general formula (1) includes:

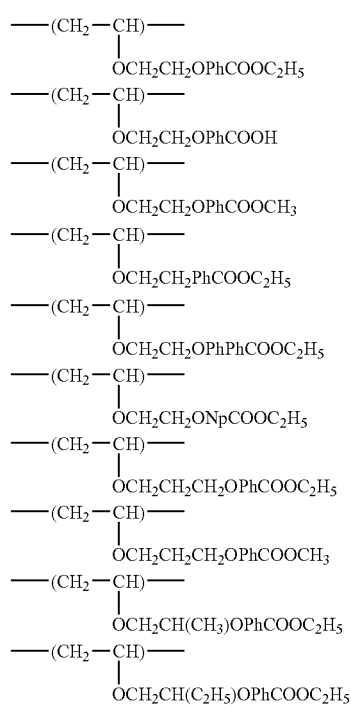

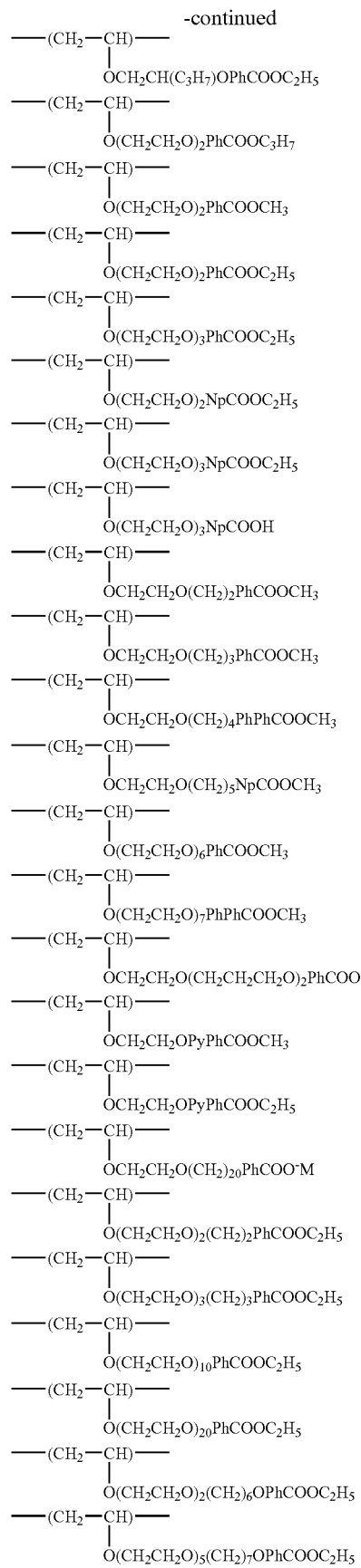

wherein Ph is 1,4-phenylene or 1,3-phenylene; Py is 2,5-pirimidylene; 2,5-Pyr is pyridylene; and Np is 2,6-naphthylene, 1,4-naphthylene or 1,5-naphthylene.

In the general formula (1), preferably A is an alkylene group preferably of a carbon number of 2 to 10, and may be substituted with methyl, ethyl, propyl, phenyl or the like;

m is an integer preferably of 1 to 10;

B is methylene, ethylene, propylene, butylenes, pentylene, hexylene, heptylene, octylene or the like; D is phenylene, pyridylene, pirimidylene, naphthylene, anthranylene, phenanthranylene, thiophenylene, furanylene or the like;

n is an integer of 1 to 5; and

R is an alkyl group of a carbon number of 1 to 10, or an aromatic ring such as phenyl, pyridyl, biphenyl group or the like which may be substituted with an alkyl, alkoxy group, or the like.

The repeating monomer unit represented by the general formula (1) is more preferably the one represented by the general formula (6):

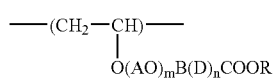

General Formula (6)

wherein A is ethylene or propylene; m is an integer of 0 to 5, and when m is 2 or more, A may be different with each other; B is a single bond or alkylene of 1 to 5 carbon atoms; D is phenylene or naphthylene; n is an integer of 1 to 5, and when n is 2 or more, D may be different at each occurrence; and R is hydrogen, alkyl or phenyl.

The monomer unit represented by the general formula (1) has a side chain being an aromatic carboxylic acid derivative. Since aromatic carboxylic acid derivatives are different from aliphatic carboxylic acid derivatives in acidity, the above monomer structure is very useful because it can provide various functional compositions containing polyvinyl ether polymer materials of different acidity.

The polymer compound comprising monomer units represented by the general formula (1) can be obtained by polymerization of a vinyl ether compound having a corresponding substituent. Usually, polymerization is carried out by cationic polymerization. As a polymerization initiator, protonic acids such as hydrochloric, sulfuric, methanesulfonic, trifluoroacetic, trifluoromethanesulfonic and perchloric acid; Lewis acids such as $BF_3$, $AlCl_3$, $TiCl_4$, $SnCl_4$, $FeCl_3$, $RAlCl_2$ or $R_{1.5}AlCl_{1.5}$, where R is an alkyl, in combination with a cation source such as protonic acid, water, alcohol or adduct of vinyl ether and carboxylic acid. The polymer compound can be produced by polymerization of a vinyl ether compound in the presence of such a polymerization initiator.

The polymer compound comprising monomer units represented by the general formula (1) has a number-average molecular weight of 200 to 10,000,000, preferably 1000 to 1,000,000. Those having a molecular weight above 10,000,000 may not be readily dispersed in a solvent, because of excessive entanglement within or between the polymer chains, and those of a molecular weight below 200 may not exhibit full steric effect of a polymer compound due to too small molecular weight. The polymer compound of the present invention may be a homopolymer comprising a single monomer unit or copolymer comprising two or more monomer units. In the case of copolymer, it contains a monomer unit represented by the general formula (1) preferably at 1% by mole or more, more preferably 3% by mole or more. When the content of the monomer unit represented by the general formula (1) is lower than 1% by mole, functions such as dispersion improvement may not be satisfactorily exhibited. Preferably, the copolymer contains vinyl ether monomer units 50% by mole or more of the monomer units, more preferably 80% by mole or more.

<Polymer Compound Contained in the Second Aspect of the Present Invention>

A polymer compound to be contained in the second aspect of the present invention, which comprises monomer units represented by the general formula (2), is described in detail.

Specific examples of the monomer units represented by the general formula (2) include:

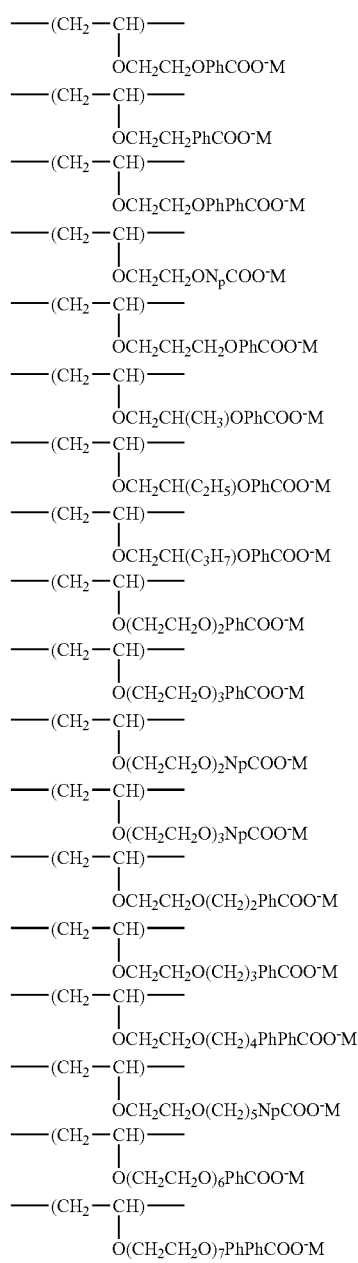

-continued

—(CH₂—CH)—
    |
    OCH₂CH₂O(CH₂CH₂CH₂O)₂PhCOO⁻M

—(CH₂—CH)—
    |
    OCH₂CH₂OPyPhCOO⁻M

—(CH₂—CH)—
    |
    OCH₂CH₂O(CH₂)₂₀PhCOOCH₃

—(CH₂—CH)—
    |
    O(CH₂CH₂O)₂(CH₂)₂PhCOO⁻M

—(CH₂—CH)—
    |
    O(CH₂CH₂O)₃(CH₂)₃PhCOO⁻M

—(CH₂—CH)—
    |
    O(CH₂CH₂O)₁₀PhCOO⁻M

—(CH₂—CH)—
    |
    O(CH₂CH₂O)₂₀PhCOO⁻M

—(CH₂—CH)—
    |
    O(CH₂CH₂O)₂(CH₂)₆OPhCOO⁻M

—(CH₂—CH)—
    |
    O(CH₂CH₂O)₅(CH₂)₇OPhCOO⁻M

—(CH₂—CH)—
    |
    O(CH₂CH₂O)₆(CH₂)₈OPhCOO⁻M

—(CH₂—CH)—
    |
    O(CH₂CH₂O)₁₀(CH₂)₁₀OPhCOO⁻M

—(CH₂—CH)—
    |
    O(CH₂CH₂O)₁₅(CH₂)₁₅OPhCOO⁻M

—(CH₂—CH)—
    |
    O(CH₂CH₂O)₂(CH₂)₂₀OPhCOO⁻M

—(CH₂—CH)—
    |
    OCH₂CH₂CH₂CH₂CH₂CH₂CH₂CH₂O(CH₂)₂OPhCOO⁻M

—(CH₂—CH)—
    |
    OCH₂CH₂CH₂CH₂O(CH₂)₃OPhCOO⁻M

—(CH₂—CH)—
    |
    OCH₂CH₂CH₂CH₂O(CH₂)₄OPhCOO⁻M

—(CH₂—CH)—
    |
    OCH₂CH₂CH₂CH₂CH₂CH₂CH₂CH₂O(CH₂)₅OPhCOO⁻M

—(CH₂—CH)—
    |
    OCH₂CH₂CH₂CH₂CH₂CH₂O(CH₂)₆OPhCOO⁻M

—(CH₂—CH)—
    |
    OCH(CH₃)CH₂O(CH₂)₇OPhCOO⁻M

—(CH₂—CH)—
    |
    OCH(CH₃)CH₂O(CH₂)₈OPhCOO⁻M

—(CH₂—CH)—
    |
    OCH₂CH(CH₃)O(CH₂)₁₀OPhCOO⁻M

—(CH₂—CH)—
    |
    OCH(C₂H₅)CH₂O(CH₂)₁₅OPhCOO⁻M

—(CH₂—CH)—
    |
    OCH₂CH(CH₃)O(CH₂)₂₀OPhCOO⁻M

—(CH₂—CH)—
    |
    OCH₂CH₂O(CH₂)₂OPhCOO⁻M

-continued

—(CH₂—CH)—
    |
    OCH₂CH₂O(CH₂)₃OPhCOO⁻M

—(CH₂—CH)—
    |
    OCH₂CH₂O(CH₂)₄OPhCOO⁻M

—(CH₂—CH)—
    |
    OCH₂CH₂CH₂CH₂O(CH₂)₅OPyrCOO⁻M

—(CH₂—CH)—
    |
    OCH₂CH₂O(CH₂)₆OPhCOO⁻M

—(CH₂—CH)—
    |
    O(CH₂CH₂O)₂(CH₂)₇OPhCOO⁻M

—(CH₂—CH)—
    |
    OCH₂CH₂O(CH₂)₈OPhCOO⁻M

—(CH₂—CH)—
    |
    OCH₂CH₂O(CH₂)₁₀OPhCOO⁻M

—(CH₂—CH)—
    |
    OCH₂CH₂O(CH₂)₁₅OPhCOO⁻M

—(CH₂—CH)—
    |
    OCH₂CH₂O(CH₂)₂₀OPhCOO⁻M wherein Ph is 1,4-phenylene or 1,3-phenylene; Py is 2,5-pirimidylene; 2,5-Pyr is pyridylene; and Np is 2,6-naphthylene, 1,4-naphthylene or 1,5-naphthylene.

Preferably, in the general formula (2), the alkylene group represented by A has a carbon number of 2 to 10, and may be substituted with methyl, ethyl, propyl, phenyl or the like;

m is an integer preferably of 1 to 10;

B is methylene, ethylene, propylene, butylenes, pentylene, hexylene, heptylene, octylene or the like;

D is phenylene, pyridylene, pirimidylene, naphthylene, anthranylene, phenanthranylene, thiophenylene, furanylene or the like;

n is an integer preferably of 1 to 5; and

M is a monovalent metal cation such as sodium, potassium or lithium, or a polyvalent metal cation such as magnesium, calcium, nickel and iron. When M is a polyvalent metal cation, it forms an ion pair with 2 or more $COO^{31}$ anions.

The repeating monomer unit represented by the general formula (2) is more preferably the one represented by the general formula (7):

General Formula (7)

—(CH₂—CH)—
    |
    O(AO)ₘB(D)ₙCOO⁻M wherein A is ethylene or propylene; m is an integer of 0 to 5, and when m is 2 or more, A may be different each other; B is a single bond or alkylene of 1 to 5 carbon atoms; D is phenylene or naphthylene; n is an integer of 1 to 5, and when n is 2 or more, D may be different at each occurrence; and M is a mono- or poly-valent metal cation.

The polymer compound comprising monomer units represented by the general formula (2) can be produced by alkaline hydrolysis of the side chain ester segment of a polymer compound comprising the corresponding monomer units represented by the general formula (1). It may be also produced by acid hydrolysis followed by alkali treatment. However, the former process is preferable.

The polymer compound comprising monomer units represented by the general formula (2) has a number-average molecular weight of 200 to 10,000,000, preferably 1000 to 1,000,000. Those having a molecular weight above 10,000,000 may not be readily dispersed in a solvent, because of excessive entanglement within or between the polymer chains, and those of a molecular weight below 200 may not exhibit full steric effect of a polymer compound due to too small molecular weight. The polymer compound of the present invention may be a homopolymer comprising a single monomer unit or copolymer comprising two or more monomer units. In the case of copolymer, it contains a monomer unit represented by the general formula (2) preferably at 1% by mole or more, more preferably 3% by mole or more. When the content of the monomer unit represented by the general formula (2) is lower than 1% by mole, functions such as dispersion improvement may not be satisfactorily exhibited. Preferably, the copolymer contains vinyl ether monomer units 50% by mole or more of the monomer units, more preferably 80% by mole or more.

<Compositions of the First and Second Aspects>

The composition of the present invention comprises a polymer compound comprised of monomer units represented by the general formula (1) or (2), and a solvent or a binder resin.

The composition of the present invention preferably further contains a polymer compound, a colorant or a functional material having an intended function, where the polymer compound works to disperse the colorant or the functional material. The colorant or functional material is preferably granular solid. Such granular solid useful for the present invention includes pigments, metals, herbicides, insecticides biomaterials and medicine.

The functional material for the composition of the invention may be the polymer compound of the present invention per se, or may be another compound. It is preferably incorporated normally at 0.1 to 50% by weight of the whole composition of the present invention. It may be a soluble material, or a dye or molecular catalyst.

The polymer compound having a monomer unit represented by the general formula (1) or (2) is incorporated preferably at 0.5 to 90% by weight of the whole composition of the present invention, more preferably 1 to 60%, still more preferably 2 to 50%. It may be insufficient in dispersion stability below 0.5%, and may be excessively viscous above 70%.

The composition of the present invention also comprises a solvent or binder resin. A solvent or binder resin is incorporated at 1 to 98% by weight, preferably 10 to 96%, still more preferably 20 to 95% of the composition. The dispersion stability of the functional material or polymer compound may be insufficient when the content of the solvent or binder resin is below 1%, and function thereof may not fully exhibit when its function the content of the solvent or binder resin is higher than 98%.

<Block Polymer Compound>

The polymer compound comprising a monomer unit represented by the general formula (1) or (2) is preferably a block compound.

Amphipathic property is one of the favorable properties of such a block polymer compound. This property can be realized when a compound has a hydrophobic and hydrophilic block segments simultaneously. The block polymer compound of the present invention can form micelles in an aqueous solvent, when it is amphipathic. Such an amphipathic, polymer compound can make a recording material of favorable properties, as described later.

In general, when a polymer is used to improve dispersion stability and inclusion properties of a functional material, it is preferable that the polymer is more flexible in molecular motion, because it can physically entwine the functional material surface to increase affinity. Moreover, flexibility is preferred due to easy formation of a coating layer on a recording medium, which is discussed later. For this reason, the main chain of the block polymer preferably has a glass transition temperature Tg of 20° C. or lower, more preferably 0° C. or lower, still more preferably −20° C. or lower. Satisfactorily, polymers of polyvinyl ether structure possess a low glass transition temperature and flexible characteristics. Most of the above monomer units have a glass transition temperature of around −20° C. or lower.

The composition of the present invention comprises the polymer compound, a colorant or functional material having an intended function, where the block polymer compound works to disperse the colorant or functional material. The colorant or functional material can be liquid or solid including a soluble material, oil, pigment, metal, herbicide, insecticide, biomaterial, medicine, dye and molecular catalyst.

Another aspect of the present invention is a composition comprising a block polymer, a solvent or dispersion medium, and a colorant, wherein the block polymer has a polyvinyl ether monomer unit selected from the group consisting of a carboxylate ester, carboxylic acid or carboxylate. The monomer unit of carboxylate ester, carboxylic acid or carboxylate is preferably represented by the general formula (1) or (2), although not limited thereto.

The other structural examples include:

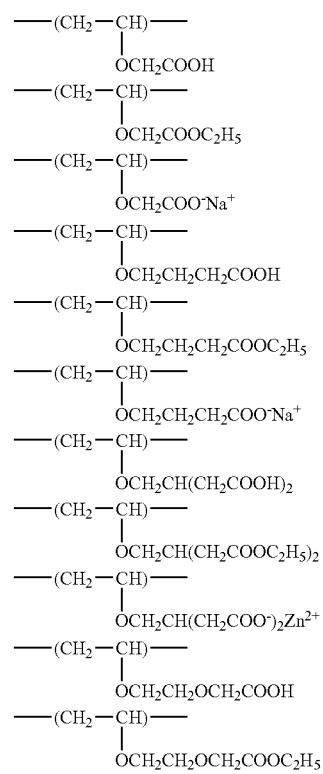

-continued

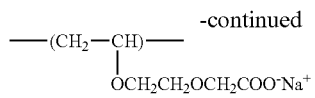

A functional material for the composition of the present invention is incorporated at 0.01 to 90% by weight of the composition of the present composition, preferably 0.1 to 50%.

In the composition of the present invention, the block copolymer comprising monomer units represented by the general formula (1) or (2) is contained at 0.2 to 99% by weight of the composition, preferably 0.5 to 70%. This content holds also for the block polymer compound having a monomer unit of carboxylate ester, carboxylic acid or carboxylate.

<Recording Material of the Third Aspect of the Present Invention>

The third aspect of the present invention is a recording material containing a composition comprising the polymer compound, solvent or dispersion medium, and colorant.

Specific examples of the recording material are a toner composition comprising a dispersion medium (e.g., binder resin), a colorant and a polymer compound, and an ink composition comprising a solvent, a colorant and a polymer compound, wherein the polymer compound comprises the monomer units represented by the general formula (1) or (2).

[Ink Composition]

First, the ink composition being one of the preferred embodiments of the present invention is described.

The content of the polymer compound comprising monomer units represented by the general formula (1) or (2) is 0.1 to 90% by weight, preferably 1 to 80%, of the ink composition. The content is preferably 1 to 30% by weight, when used for ink-jet printing.

Components of the ink composition other than the polymer compound are described in detail below including water, aqueous solvent, colorant and additives.

[Water]

Water is preferably ion-exchanged water, pure water or superpure water from which metal ions etc. have been removed.

[Aqueous Solvent]

The aqueous solvent useful for the present invention includes polyhydric alcohols such as ethylene glycol, diethylene glycol, triethylene glycol, polyethylene glycol, propylene glycol, polypropylene glycol and glycerin; polyhydric alcohol ethers such as ethylene glycol monomethyl ether, ethylene glycol monoethyl ether, ethylene glycol monobutyl ether, diethylene glycol monoethyl ether and diethylene glycol monobutyl ether; and nitrogen-containing solvents such as N-methyl pyrrolidone, substituted pyrrolidone and triethanolamine. Monohydric alcohol such as methanol, ethanol and isopropyl alcohol can be used to accelerate drying of the ink on the recording medium.

Water and aqueous solvent are incorporated preferably at 20 to 95%, more preferably 30 to 90%, by weight of the ink composition of the present invention. Organic solvent such as toluene, ethyl acetate, acetone or methylethylketone may be incorporated in place of water and aqueous solvent.

[Colorant]

The ink composition of the present invention also contains a colorant such as pigment and dye, preferably pigment. Specific examples of pigment and dye useful for the present invention are described below.

Pigment can be either organic or inorganic. Pigments preferably used for ink are pigments of black and three primary colors of cyan, magenta and yellow. Also, other pigments, e.g., pigments of other colors, colorless or pale colored pigments, pigments of metal luster may be used. New pigments synthesized for the present invention may be also used.

Followings are examples of commercially available pigments of black, cyan, magenta, and yellow.

Examples of black pigments include, but not limited to, Raven 1060, Raven 1080, Raven 1170, Raven 1200, Raven 1250, Raven 1255, Raven 1500, Raven 2000, Raven 3500, Raven 5250, Raven 5750, Raven 7000, Raven 5000 ULTRA II, Raven 1190 ULTRA II (all of the above, manufactured by Columbian Carbon Co.), Black Pearls L, MOGUL-L, Regal 400R, Regal 660R, Regal 330R, Monarch 800, Monarch 880, Monarch 900, Monarch 1000, Monarch 1300, Monarch 1400 (all of the above, manufactured by CABOT CORPORATION), Color Black FW1, Color Black FW2, Color Black FW200, Color Black 18, Color Black S160, Color Black S170, Special Black 4, Special Black 4A, Special Black 6, Printex 35, Printex U, Printex 140U, Printex V, Printex 140V (all of the above, manufactured by Degussa AG), No. 25, No. 33, No. 40, No. 47, No. 52, No. 900, No. 2300, MCF-88, MA600, MA7, MA8, MA100 (all of the above, manufactured by MITSUBISHI CHEMICAL CORPORATION).

Examples of cyan pigments include, but not limited to, C.I. Pigment Blue-1, C.I. Pigment Blue-2, C.I. Pigment Blue-3, C.I. Pigment Blue-15, C.I. Pigment Blue-15:2, C.I. Pigment Blue-15:3, C.I. Pigment Blue-15:4, C.I. Pigment Blue-16, C.I. Pigment Blue-22, C.I. Pigment Blue-60.

Examples of magenta pigments include, but not limited to, C.I. Pigment Red-5, C.I. Pigment Red-7, C.I. Pigment Red-12, C.I. Pigment Red-48, C.I. Pigment Red-48:1, C.I. Pigment Red-57, C.I. Pigment Red-112, C.I. Pigment Red-122, C.I. Pigment Red-123, C.I. Pigment Red-146, C.I. Pigment Red-168, C.I. Pigment Red-184, C.I. Pigment Red-202, C.I. Pigment Red-207.

Examples of yellow-pigments include, but not limited to, C.I. Pigment Yellow-12, C.I. Pigment Yellow-13, C.I. Pigment Yellow-14, C.I. Pigment Yellow-16, C.I. Pigment Yellow-17, C.I. Pigment Yellow-74, C.I. Pigment Yellow-83, C.I. Pigment Yellow-93, C.I. Pigment Yellow-95, C.I. Pigment Yellow-97, C.I. Pigment Yellow-98, C.I. Pigment Yellow-114, C.I. Pigment Yellow-128, C.I. Pigment Yellow-129, C.I. Pigment Yellow-151, C.I. Pigment Yellow-154.

The composition of the present invention may also contain a self-dispersing pigment dispersible in water. Such pigments fall into two types, those covered with adsorbed polymer for steric hindrance effect, and those utilizing electrostatic repulsion effect. The commercial products include CAB-O-JET200 and CAB-O-JET300 (Cabot Corporation), and Microjet Black CW-1 (Orient Chemical Industries).

The pigment for the ink composition of the present invention is incorporated preferably at 0.1 to 50% by weight of the ink composition. Content lower than 0.1% may not give a sufficient image concentration, and content higher than 50% may deteriorate fixation properties of the image. More preferable content is 0.5 to 30% by weight.

Also dye can be used for the ink composition of the present invention. Dyes useful for the present invention include direct, acidic, basic and reactive dyes, water-soluble dyes for food coloring and insoluble dispersion dyes.

For example, oil-soluble dyes may be C.I. Solvent Blue-33, -38, -42, -45, -53, -65, -67, -70, -104, -114, -115, -135; C.I. Solvent Red-25, -31, -86, -92, -97, -118, -132, -160, -186, -187, -219; C.I. Solvent Yellow-1, -49, -62, -74, -79, -82, -83, -89, -90, -120, -121, -151, -153, -154.

For example, water-soluble dyes may be direct dyes such as C.I. Direct Black-17, -19, -22, -32, -38, -51, -62, -71, -108, -146, -154; C.I. Direct Yellow-12, -24, -26, -44, -86, -87, -98, -100, -130, -142; C.I. Direct Red, -1, -4, -13, -17, -23, -28, -31, -62, -79, -81, -83, -89, -227, -240, -242, -243; C.I. Direct Blue-6, -22, -25, -71, -78, -86, -90, -106, -199; C.I. Direct Orange-34, -39, -44, -46, -60; C.I. Direct Violet-47, -48; C.I. Direct Brown-109; C.I. Direct Green-59, acid dyes such as C.I. Acid Black-2, -7, -24, -26, -31, -52, -63, -112, -118, -168, -172, -208; C.I. Acid Yellow-11, -17, -23, -25, -29, -42, -49, -61, -71; C.I. Acid Red-1, -6, -8, -32, -37, -51, -52, -80, -85, -87, -92, -94, -115, -180, -254, -256, -289, -315, -317; C.I. Acid Blue-9, -22, -40, -59, -93, -102, -104, -113, -117, -120, -167, -229, -234, -254: C.I. Acid Orange-7, -19; C.I. Acid Violet-49, reactive dyes such as C.I. Reactive Black-1, -5, -8, -13, -14, -23, -31, -34, -39; C.I. Reactive Yellow-2, -3, -13, -15, -17, -18, -23, -24, -37, -42, -57, -58, -64, -75, -76, -77, -79, -81, -84, -85, -87, -88, -91, -92, -93, -95, -102, -111, -115, -116, -130, -131, -132, -133, -135, -137, -139, -140, -142, -143, -144, -145, -146, -147, -148, -151, -162, -163; C.I. Reactive Red-3, -13, -16, -21, -22, -23, -24, -29, -31, -33, -35, -45, -49, -55, -63, -85, -106, -109, -111, -112, -113, -114, -118, -126, -128, -130, -131, -141, -151, -170, -171, -174, -176, -177, -183, -184, -186, -187, -188, -190, -193, -194, -195, -196, -200, -201, -202, -204, -206, -218, -221; C.I. Reactive Blue-2, -3, -5, -8, -10, -13, -14, -15, -18, -19, -21, -25, -27, -28, -38, -39, -40, -41, -49, -52, -63, -71, -72, -74, -75, -77, -78, -79, -89, -100, -101, -104, -105, -119, -122, -147, -158, -160, -162, -166, -169, -170, -171, -172, -173, -174, -176, -179, -184, -190, -191, -194, -195, -198, -204, -211, -216, -217; C.I. Reactive Orange-5, -7, -11, -12, -13, -15, -16, -35, -45, -46, -56, -62, -70, -72, -74, -82, -84, -87, -91, -92, -93, -95, -97, -99; C.I. Reactive Violet-1, -4, -5, -6, -22, -24, -33, -36, -38; C.I. Reactive Green-5, -8, -12, -15, -19, -23; C.I. Reactive Brown-2, -7, -8, -9, -11, -16, -17, -18, -21, -24, -26, -31, -32, -33, C.I. Basic Black-2; C.I. Basic Red-1, -2, -9, -12, -13, -14, -27; C.I. Basic Blue-1, -3, -5, -7, -9, -24, -25, -26, -28, -29; C.I. Basic Violet-7, -14, -27; C.I. Food Black-1, -2.

The above-described colorant examples are preferable for the ink composition of the present invention. However, the useful ones for the present invention are not limited to the above. The content of a dye in the ink composition of the present invention is preferably 0.1 to 50% by weight of the ink.

[Additives]

The composition of the present invention may contain various additives or auxiliary agents as required. One of the additives useful for the present invention is a dispersion stabilizer, which stably disperses the pigment in the solvent. The composition of the present invention can disperse granular solid such as pigment due to the polyvinyl ether polymer contained therein. However, it may contain another dispersion stabilizer, when its dispersion capacity is insufficient.

As a dispersion stabilizer which can be added to the composition of the present invention, there are resins and surfactants having both hydrophilic and hydrophobic segments therein. Examples of such amphiphilic resins include a copolymer of hydrophilic and hydrophobic monomers.

Hydrophilic monomers useful for the present invention include acrylic, methacrylic, maleic and fumaric acid, the carboxylate monoesters described earlier, vinylsulfonic and styrenesulfonic acid, acrylamide, and methacryloxyethyl phosphate or the like. Hydrophobic monomers useful for the present invention include styrene and its derivatives, e.g., styrene and α-methylstyrene; and vinyl cyclohexane, vinylnaphthalene derivative, acrylate esters and methacrylate esters. Copolymers of various structures, such as random, block or graft copolymers may be used for the present invention. Needless to say, the hydrophilic and hydrophobic monomers useful for the present invention are not limited to the above.

The surfactant for the present invention may be anionic, nonionic, cationic or ampholytic. The anionic surfactants useful for the present invention include fatty acid salts, alkyl sulfate ester salts, alkylarylsulfonic acid salts, alkyldiaryl ether disulfonic acid salts, dialkylsulfosuccinic acid salts, alkyl phosphoric acid salts, naphthalene/formalin sulfonate condensate, polyoxyethylene alkyl phosphate ester salts and glycerol borate fatty acid esters. The nonionic surfactants useful for the present invention include polyoxyethylene alkyl ether, polyoxyethyleneoxypropylene block copolymer, sorbitan/fatty acid ester, glycerin/fatty acid ester, polyoxyethylene/fatty acid ester, polyoxyethylenealkylamine, and fluorine- and silicon-based ones. The cationic surfactants useful for the present invention include alkylamine salts, quarternary ammonium salts, alkyl pirydinium salts and alkyl imidazolium salts. The ampholytic surfactants useful for the present invention include alkyl betaine and alkylamine oxide and phosphatidyl choline. The surfactants useful for the present invention are also not limited to the above.

The other additives to the ink composition of the present invention include a pH adjustor for stabilizing the ink and securing stability of the ink in a flow path of the recording apparatus, a penetration agent for accelerating penetration of the ink into the recording medium and thereby accelerating apparent drying of the ink, an antifungal agent to protect the ink from molds, a chelating agent for sequestering metal ions in the ink and preventing metal deposition in the nozzle or deposition of insolubles in the ink, an antifoaming agent for preventing foaming of the ink during circulation, migration or production of the ink, an antioxidant, a viscosity adjustor, an antistatic agent and a UV absorber.

The ink composition of the present invention can be produced by mixing and uniformly dissolving or dispersing the above components. For example, two or more components are mixed with each other, and pulverized and dispersed by using a sand mill, ball mill, homogenizer or nanomizer to prepare the ink base liquid, whose properties are adjusted with a solvent or additives.

Next, the toner composition of the present invention is described. More specifically, the toner composition comprises a dispersion medium such as a binder resin, a colorant and a polymer compound comprising monomer units represented by the general formula (1) or (2).

The polymer compound is incorporated at 0.1 to 50% by weight in the toner composition of the present invention, preferably 0.5 to 30%.

The polymer compound for the present invention can be used as the binder resin itself, or may be used in combination with a binder resin such as styrene acrylic resin and polyester resin.

The components other than the polymer compound for the toner composition of the present invention are described below in detail. These components include binder resins, colorants (pigment or dye), charge controlling agents, releasing agents, external additives and magnetic powder.

[Other Components for the Toner Composition]

The binder resin useful for the toner composition includes styrene acrylic copolymer, polyester and polycarbonate. Binder resin content is preferably 10 to 99% by weight. As the colorant, the pigments and dyes described earlier for the ink composition can be also used. It is incorporated preferably at 0.1 to 50% by weight. The charge controlling agents useful for the present invention include metal/azo complexes, triphenylmethane-based dyes, nigrosine and ammonium salts. It is incorporated preferably at 0.1 to 30% by weight. The releasing agents useful for the present invention include synthetic wax and natural wax. The external additives useful for the present invention include finely pulverized inorganic materials, e.g., silica, alumina and titana; and finely pulverized resins, e.g., polyvinylidene fluoride (PVDF) and polytetrafluoroethylene. The magnetic powders useful for the present invention include those of magnetite, hematite and ferrite. The toner composition of the present invention can work if not all of these components are contained, and it may contain other components.

The toner composition of the present invention can be produced by mixing the above components, melting/kneading them to a uniform mixture, finely pulverizing the mixture by a speed mill or jet mill, and classifying the resulting particles to obtain toner particles of an intended size. The toner composition can be produced by mixing the resulting toner particles with external additives by a mixer.

The composition of the first or second aspect of the present invention can have various uses in addition to the toner or ink compositions. When the composition contains a colorant, the colorant is preferably encapsulated in a block polymer compound that is characteristically used in the present invention, in view of suppression of weather deterioration of the colorant. In the case of a water-soluble ink, an oil-soluble colorant or colorant particles with hydrophobic surface can be included in the micelles of the block polymer compound rather easily.

Next, the method for thickening the composition of the present invention is described. The composition of the first or second aspect of the present invention becomes thick in contact with hydrogen ions or metal cations. Typically, a solution of the polymer of the first aspect of the present invention and a functional material, which is in a dispersed or micellar condition in an aqueous solution, is brought into contact with hydrogen ion or polyvalent metal cations such as zinc, aluminum, calcium, barium and nickel to agglomerate the dispersion or dispersed micellar particles. The thickening method preferably involves agglomeration of the micellar polymer compound. Since the polymer has ionized carboxylic acid salt etc., the ionic functional groups are neutralized in contact with a sufficient quantity of hydrogen ion or metal cation, to sharply increase affinity between the micelles to greatly increase viscosity. This method is preferably applicable to an ink composition. When an ink composition is applied to fixed on a recording medium, ink thickening can provide excellent fixation properties. The thickening method is suitably applicable to the image-forming method and apparatus described below.

The composition of the present invention can be thickened by contacting it to a hydrogen ion or polyvalent metal cation solution, or to a medium coated beforehand with hydrogen ion or polyvalent metal cation. The amount of hydrogen ion or polyvalent metal cation is be contacted or added is in the range of 0.01 to 100 mole equivalents of the ionic group of the polymer compound, preferably 0.05 to 50 mole equivalents.

Alternatively, the composition of the present invention may thicken in response to stimulation. By applying stimulation in the process of image formation to increase viscosity, good fixation can be achieved. The stimulus may be selected from those suitable for image formation, e.g., temperature, pH, concentration, electromagnetic wave, and a combination thereof.

Next, the image-forming method and apparatus which use the ink or toner composition of the present invention are described.

[Image-forming Method and Apparatus]

The ink composition of the present invention is applicable to a variety of image-forming methods, e.g., various printing methods, ink-jet method and electrophotography, and also to an apparatus with which it can form images based on the above methods.

The image-forming method of the present invention can produce good images by the aid of the composition of the present invention. One of the preferred embodiments of the image-forming method of the present invention is an ink jet method that discharges the ink composition of the present invention from an ink discharge nozzle onto a recording medium to form an image thereon. One of the preferred methods is an ink-jet method that utilizes thermal energy to discharge ink from the nozzle.

Various types of ink-jet printers can use the composition of the present invention. These include a piezo-electric ink-jet type with a piezo-electric apparatus, and thermal ink-jet type, which gives a thermal energy to the ink to be foamed.

An ink-jet recording apparatus is outlined by referring to FIG. 1. It should be understood that the apparatus shown in FIG. 1 is for illustrating but not for limiting the present invention.

FIG. 1 is a block diagram illustrating the structure of an ink-jet recording apparatus.

The apparatus shown in FIG. 1 does recording on a recording medium moving the head. Referring to FIG. 1, the motors 56 and 58 responsible for driving the head 70 in the X and Y directions, respectively, are linked to the CPU 50, which commands all actions in the apparatus, via the circuits 52 and 54 for driving each motor. The CPU 50 instructs the motors 56 and 58 via the circuits 52 and 54 to drive the head 70 in the X and y directions to a given position on the recording medium.

As shown in FIG. 1, the head-driving circuit 60 is also linked to the head 70, in addition to the motors 56 and 58 for driving the head in the respective X and Y direction, to drive the head 70 for a given action, e.g., discharging the ink, following the instruction from the CPU 50. The CPU 50 receives information of the head 70 position from the X encoder 62 and Y encoder 64 responsible for detecting the head position, which are also linked to the CPU 50. A control program is inputted in the program memory 66. The CPU 50 drives the head 70, based on the control program and position information from the X encoder 62 and Y encoder 64, to a desired position on the recording medium, and instructs the head to discharge the ink at that position. The apparatus forms a desired image on the recording medium in the above manner. For the image-forming apparatus which can hold 2 or more types of inks for ink-jet, the above procedure is repeated necessary times with each ink to produce a given image on the recording medium.

The head 70 can be also moved after it has discharged the ink as required, to a position where a means (not shown) for removing surplus ink deposited on the head is provided, to be cleaned by proper wiping means. Specific cleaning means may be selected from the conventional means used for the above purpose.

On completion of the above image-forming procedure, the recorded medium is replaced by a new medium by a recording medium conveying mechanism, which is not shown.

The above embodiment can be modified or varied within scope of the present invention. For example, the head 70 is moved in the X and Y directions in the above embodiment. However, it may be designed to move only in X (or Y) direction with the recording medium moving in Y (or X) direction, to form image.

According to the present invention, an ink jet recording head provided with means (e.g., an electro-thermal converting element or a laser) for generating thermal energy to discharge the ink brings the excellent effect. Such a system can produce precision images. The image quality can be further improved when the ink composition of the present invention is used in thermal ink jet recording.

The representative structures of and working principles for the apparatus provided with a means for generating thermal energy, e.g., the one described above, are preferably based on the basic principles disclosed by, e.g., Patent Documents 1 and 2. These apparatuses are applicable either to the so-called on-demand or continuous type. The apparatus. of the present invention is particularly effective when applied to the on-demand type, because the liquid is securely held, and at least one type of driving signal, which corresponds to the discharge information, is applied to the electro-thermal converting element positioned in the flow path to generate thermal energy and increase temperature rapidly enough to cause at least nuclear boiling. This thermal energy causes film boiling on the heater board in the head, on which bubbles are formed by the action of heat according to the signals in one-to-one response. The liquid is discharged from the discharge port by expansion/shrinkage of the foams, to form at least one droplet. The pulsed driving signal is more preferable, because it immediately causes expansion/shrinkage of the foams, achieving quicker response for discharging the liquid. The pulse driving signals described in Patent Documents 3 or 4 are preferable. More excellent discharge can be done under the conditions concerning temperature-increasing rate on the heater described in Patent Document 5.

In addition to the head structure described in above Patent Documents comprising a discharge orifice, an electro-thermal converting element, and a flow path that is straight or right angle, another structure disclosed in Patent Document 6 or 7 is also included in the present invention where the heater is provided in a curved region. All of these structures are within scope of the present invention. Moreover, Patent Document 8 discloses a structure with two or more electro-thermal converters and a common slit working as the discharge port for these converters. Patent Document 9 discloses a structure provided with an opening for absorbing pressure waves caused by the thermal energy as the discharge port. These structures are also useful for the present invention. In short, the present invention can discharge the ink securely and efficiently by the head of any structure.

The image-forming apparatus of the present invention can also efficiently work, when provided with a full-line type head, which covers the maximum width of the recording medium. The head structure is not limited. For example, the maximum width can be covered by a combination of 2 or more heads, or by a single head.

Moreover, the apparatus of the present invention can also efficiently work, when provided with a serial type head, a head fixed on the apparatus body, or a chip type head that is exchangeably mounted on the apparatus body and electrically linked to and supplied with the ink from the apparatus body.

The apparatus of the present invention may be further provided with a means for removing liquid droplets. Such an apparatus can realize still more favorable discharging effect.

The apparatus of the present invention may have a structure provided with an auxiliary means. Such a structure is preferable, because it can further stabilize the effect of the present invention. The specific examples of these auxiliary means include a capping means for the head, pressurizing or evacuating means, preheating means of another electro-thermal converting element, a different heating element, or a combination thereof, and a preliminarily discharging means other than the ink discharging means.

The apparatus most effective for the present invention is that utilizing film boiling as described above.

Each port for the head of the present invention preferably discharges 0.1 to 100 picoliters of the ink.

The ink composition of the present invention can be also used for an indirect recording system in which an intermediate transfer medium is printed with the ink and the image is then transferred to a recording medium, e.g., paper. It is also applicable to a recording system which includes an intermediate transfer medium for direct printing.

<Polymerizable Compound of the Fourth Aspect>

The fourth aspect of the present invention is a compound represented by the general formula (3). This compound is described in detail below.

More specifically, the polymerizable compounds represented by the general formula (3) include:

$CH_2$=$CHOCH_2CH_2O(CH_2)_4PhPhCOOCH_3$
$CH_2$=$CHO(CH_2CH_2O)_7PhPhCOOCH_3$
$CH_2$=$CHOCH_2CH_2OPyPhCOOCH_3$
$CH_2$=$CHOCH_2CH_2OPyPhCOOC_2H_5$
$CH_2$=$CHO(CH_2CH_2O)_2(CH_2)_{20}ONpPhCOOC_2H_5$
$CH_2$=$CHOCH_2CH_2CH_2CH_2CH_2CH_2CH_2CH_2O(CH_2)_2OPhPhCOOC_2H_5$
$CH_2$=$CHOCH_2CH_2CH_2CH_2O(CH_2)_3OPhPhCOOC_2H_5$
$CH_2$=$CHOCH_2CH_2CH_2CH_2O(CH_2)_4OPhPhCOOC_2H_5$
$CH_2$=$CHOCH_2CH_2CH_2CH_2CH_2CH_2CH_2CH_2O(CH_2)_5OPhPhCOOC_2H_5$
$CH_2$=$CHOCH_2CH_2CH_2CH_2CH_2CH_2O(CH_2)_6OPhNpCOOC_2H_5$
$CH_2$=$CHOCH(CH_3)CH_2O(CH_2)_7OPhPhCOOC_2H_5$
$CH_2$=$CHOCH(CH_3)CH_2O(CH_2)_8OPhPhCOOC_2H_5$
$CH_2$=$CHOCH_2CH(CH_3)O(CH_2)_{10}OPhPhCOOC_2H_5$
$CH_2$=$CHOCH(C_2H_5)CH_2O(CH_2)_{15}OPhPhCOOC_2H_5$
$CH_2$=$CHOCH_2CH(CH_3)O(CH_2)_{20}OPhNpCOOC_2H_5$
$CH_2$=$CHOCH_2CH_2O(CH_2)_2OPhPhCOOPhH$
$CH_2$=$CHOCH_2CH_2O(CH_2)_3OPhPhPhCOOCH_2PhH$
$CH_2$=$CHOCH_2CH_2O(CH_2)_4OPhPhCOOPyrH$
$CH_2$=$CHOCH_2CH_2CH_2CH_2O(CH_2)_5OPyrPhCOOPhH$
$CH_2$=$CHOCH_2CH_2O(CH_2)_6OPhPhCOOPh(OCH_3)$
$CH_2$=$CHO(CH_2CH_2O)_2(CH_2)_7OPhPhPhCOOPh(OCH_3)$
$CH_2$=$CHOCH_2CH_2O(CH_2)_8OPhPhCOOPh(OCH_3)$
$CH_2$=$CHOCH_2CH_2O(CH_2)_{10}OPhPhCOOPh(OCH_3)$
$CH_2$=$CHOCH_2CH_2O(CH_2)_{15}OPhPhCOOPh(OCH_3)$
$CH_2$=$CHOCH_2CH_2O(CH_2)_{20}OPhPhCOOPh(OCH_3)$ wherein Ph is 1,4-phenylene or 1,3-phenylene; Py is 2,5-pirimidylene; 2,5-Pyr is pyridylene; and Np is 2,6-naphthylene, 1,4-naphthylene or 1,5-naphthylene.

In general formula (3), preferably, A is alkylene of a carbon number of 2 to 10 with or without substitution with methyl, ethyl, propyl, phenyl or the like;

m is an integer of 1 to 10;

B is an alkylene group being methylene, ethylene, propylene, butylenes, pentylene, hexylene, heptylene, or octylene;

D is phenylene, pyridylene, pirimidylene, naphthylene, anthranylene, phenanthranylene, thiophenylene or furanylene;

n is an integer of 2 to 5;

R is an alkyl group of a carbon number of 1 to 10, or an aromatic ring being phenyl, pyridyl, biphenyl group or the like with or without substitution with an alkyl, alkoxy group, or the like.

The polymerizable compound represented by the general formula (3) is more preferably the one represented by the general formula (8): General Formula (8)

$$CH_2=CHO(AO)_mB(D)_nCOOR$$

wherein A is ethylene or propylene; m is an integer of 0 to 5, and when m is 2 or more, A may be different at each occurrence; B is a single bond or alkylene of 1 to 5 carbon atoms; D is phenylene or naphthylene; n is an integer of 2 to 5, and D may be different at each occurrence; and R is a hydrogen atom, or an alkyl or phenyl group.

The polymerizable compound represented by the general formula (3) has 2 or more aromatic rings in the structure and the end of the side chain is an aromatic carboxylic acid derivative. Such a compound is advantageous in that it has high crystallinity and its purification for precision polymerization is relatively easy. Moreover, since aromatic carboxylic acid has an acidity different from that of aliphatic carboxylic acid, this polymerizable compound is very useful to provide a variety of functional polymer compounds of polyvinyl ether structure with varying acidity.

The polymerizable compound represented by the general formula (3) is typically synthesized by the etherification described below.

$$CH_2=CHOCH_2CH_2X + HOPhPhCOOC_2H_5$$
$$\downarrow \text{(base)}$$
$$CH_2=CHOCH_2CH_2OPhPhCOOC_2H_5$$

(X=halogen)

<Polymer Compound of the Fifth Aspect>

The fifth aspect of the present invention is a polymer compound comprising monomer units represented by the general formula (4). This compound is described in detail below.

More specifically, the monomer units represented by the general formula (4) include:

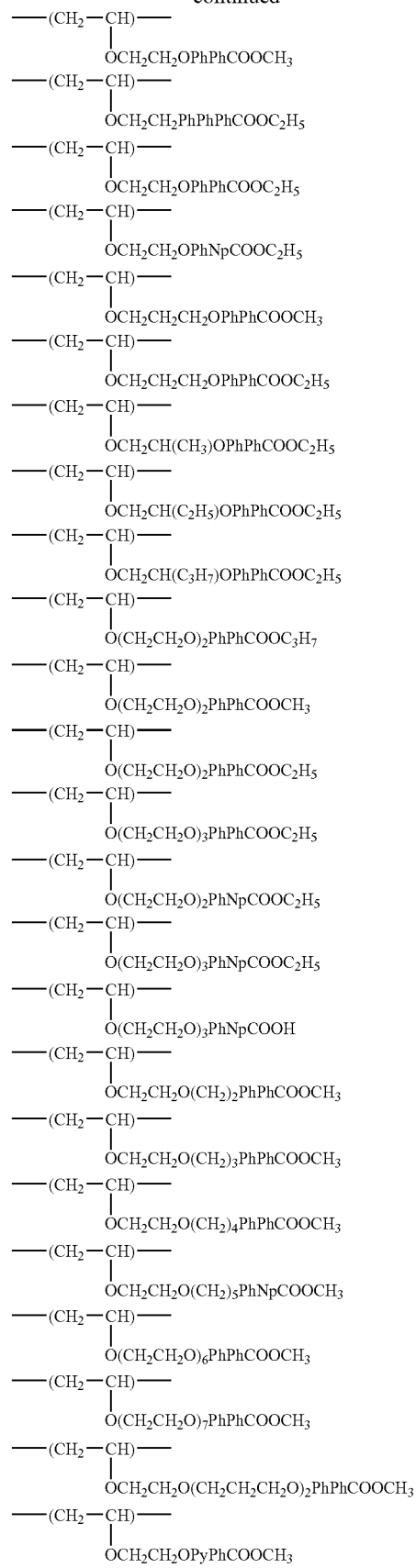

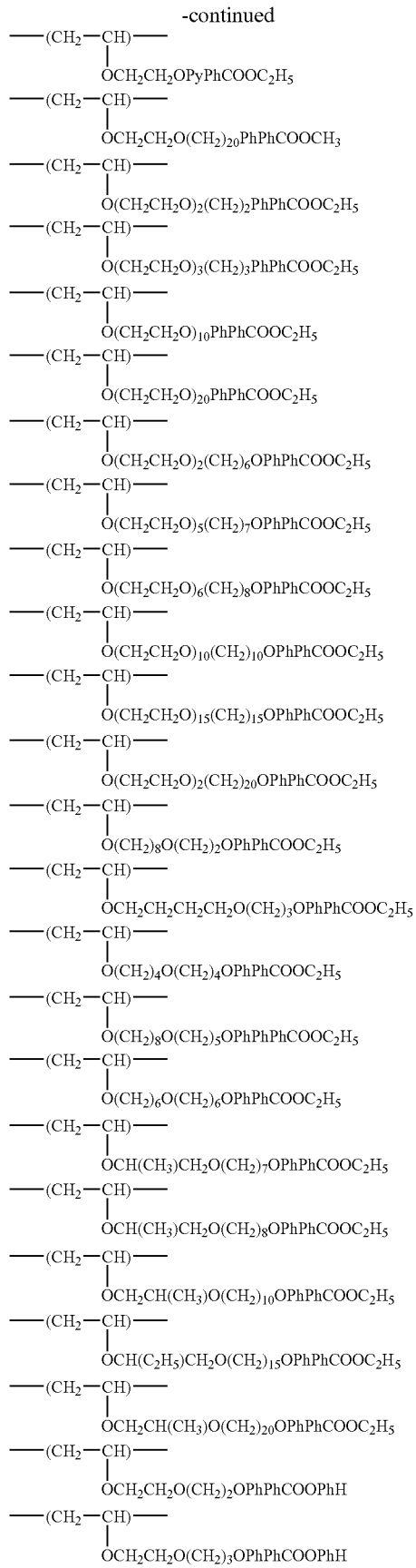

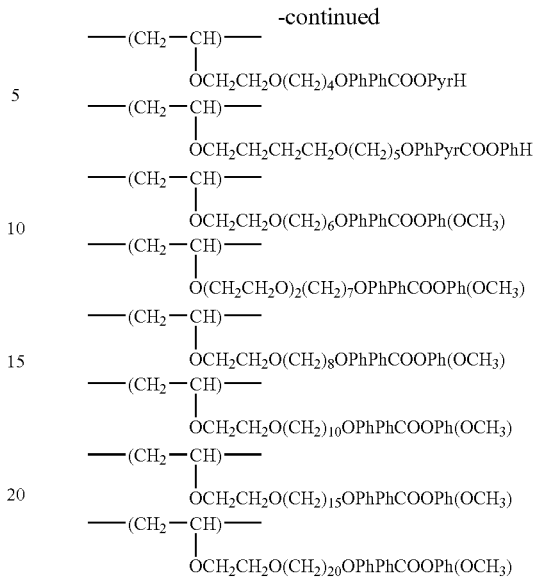

wherein Ph is 1,4-phenylene or 1,3-phenylene; Py is 2,5-pirimidylene; 2,5-Pyr is pyridylene; and Np is 2,6-naphthylene, 1,4-naphthylene or 1,5-naphthylene.

Preferably, in the general formula (4), A is an alkylene group of a carbon number of 2 to 10, with or without substitution with methyl, ethyl, propyl, phenyl or the like;

m is an integer of 1 to 10;

B as an alkylene group being methylene, ethylene, propylene, butylenes, pentylene, hexylene, heptylene, octylene or the like;

D is an aromatic ring being phenylene, pyridylene, pirimidylene, naphthylene, anthranylene, phenanthranylene, thiophenylene, furanylene or the like;

n is an integer of 2 to 5;

R is an alkyl group of a carbon number of 1 to 10, or an aromatic ring of phenyl, pyridyl, biphenyl group or the like with or without substitution with an alkyl, alkoxy group, or the like.

The repeating monomer unit represented by the general formula (4) is preferably the one represented by the general formula (9):

General Formula (9)

wherein A is ethylene or propylene; m is an integer of 0 to 5, and when m is 2 or more, A may be different; B is a single bond or alkylene of 1 to 5 carbon atoms; D is phenylene or naphthylene; n is an integer of 2 to 5, and R is a hydrogen atom, or an alkyl or phenyl group.

The compound of the present invention represented by the general formula (4) has 2 or more aromatic rings in the unit structure and the end of the side chain is an aromatic carboxylic acid salt. Aromatic carboxylic acid with 2 or more aromatic rings has an acidity different from that of an aliphatic carboxylic acid. As a result, the compound is very useful, because it provides a variety of functional polymer compounds of varying acidity with a vinyl ether monomer unit. Moreover, it can exhibit a characteristic function based on its self-organizing property because the portion of aromatic rings has very high crystallinity and high affinity with each other.

The polymer compound comprising the monomer units represented by the general formula (4) can be produced preferably by polymerization of the polymerizable compound represented by the general formula (3). This process is mainly effected by cationic polymerization in the presence of a polymerization initiator. The polymerization initiators useful for the above process include protonic acids, e.g., hydrochloric, sulfuric, methanesulfonic, trifluoroacetic, trifluoromethanesulfonic and perchloric acid; and combinations of Lewis acid (e.g., $BF_3$, $AlCl_3$, $TiCl_4$, $SnCl_4$, $FeCl_3$, $RAlCl_2$ or $R_{1.5}AlCl_{1.5}$, where R is an alkyl) and cation source (e.g., protonic acid and water, alcohol or adduct of vinyl ether and carboxylic acid). The polymer compound can be produced by the polymerization of the polymerizable compound (monomer) represented by the general formula (3) proceeding in the presence of the polymerization initiator.

The polymer compound comprising monomer units represented by the general formula (4) has a number-average molecular weight of 200 to 10,000,000, preferably 1000 to 1,000,000. Those having a molecular weight above 10,000,000 may not be readily dispersed in a solvent, because of excessive entanglement within or between the polymer chains, and those of a molecular weight below 200 may not exhibit full steric effect of a polymer compound due to too small molecular weight. The polymer compound of the present invention may be a homopolymer comprising a single monomer unit or copolymer comprising two or more monomer units. In the case of copolymer, it contains a monomer unit represented by the general formula (4) preferably at 1% by mole or more, more preferably 3% by mole or more. When the content of the monomer unit represented by the general formula (4) is lower than 1% by mole, functions such as dispersion improvement may not be satisfactorily exhibited. Preferably, the copolymer contains vinyl ether monomer units 50% by mole or more of the monomer units, more preferably 80% by mole or more.

<Polymer Compound of the Sixth Aspect>

The sixth aspect of the present invention is the polymer compound comprising monomer units represented by the general formula (5).

The specific examples of the monomer units represented by the general formula (5) include:

—($CH_2$—CH)—
|
$OCH_2CH_2PhPhCOO^-M$

—($CH_2$—CH)—
|
$OCH_2CH_2OPhPhCOO^-M$

—($CH_2$—CH)—
|
$OCH_2CH_2OPhNpCOO^-M$

—($CH_2$—CH)—
|
$OCH_2CH_2CH_2OPhPhCOO^-M$

—($CH_2$—CH)—
|
$OCH_2CH(CH_3)OPhPhCOO^-M$

—($CH_2$—CH)—
|
$OCH_2CH(C_2H_5)OPhPhCOO^-M$

-continued

—($CH_2$—CH)—
|
$OCH_2CH(C_3H_7)OPhPhCOO^-M$

—($CH_2$—CH)—
|
$O(CH_2CH_2O)_2PhPhCOO^-M$

—($CH_2$—CH)—
|
$O(CH_2CH_2O)_3PhPhCOO^-M$

—($CH_2$—CH)—
|
$O(CH_2CH_2O)_2PhNpCOO^-M$

—($CH_2$—CH)—
|
$OCH_2CH_2O(CH_2)_2PhPhCOO^-M$

—($CH_2$—CH)—
|
$OCH_2CH_2O(CH_2)_3PhPhCOO^-M$

—($CH_2$—CH)—
|
$OCH_2CH_2O(CH_2)_4PhPhCOO^-M$

—($CH_2$—CH)—
|
$OCH_2CH_2O(CH_2)_5PhNpCOO^-M$

—($CH_2$—CH)—
|
$O(CH_2CH_2O)_6PhPhCOO^-M$

—($CH_2$—CH)—
|
$O(CH_2CH_2O)_7PhPhCOO^-M$

—($CH_2$—CH)—
|
$OCH_2CH_2O(CH_2CH_2CH_2O)_2PhPhCOO^-M$

—($CH_2$—CH)—
|
$OCH_2CH_2OPyPhCOO^-M$

—($CH_2$—CH)—
|
$OCH_2CH_2O(CH_2)_{20}PhPhCOO^-M$

—($CH_2$—CH)—
|
$O(CH_2CH_2O)_2(CH_2)_2PhPhCOO^-M$

—($CH_2$—CH)—
|
$O(CH_2CH_2O)_3(CH_2)_3PhPhCOO^-M$

—($CH_2$—CH)—
|
$O(CH_2CH_2O)_{10}PhPhCOO^-M$

—($CH_2$—CH)—
|
$O(CH_2CH_2O)_{20}PhPhCOO^-M$

—($CH_2$—CH)—
|
$O(CH_2CH_2O)_2(CH_2)_6OPhPhCOO^-M$

—($CH_2$—CH)—
|
$O(CH_2CH_2O)_5(CH_2)_7OPhPhCOO^-M$

—($CH_2$—CH)—
|
$O(CH_2CH_2O)_6(CH_2)_8OPhPhCOO^-M$

—($CH_2$—CH)—
|
$O(CH_2CH_2O)_{10}(CH_2)_{10}OPhPhCOO^-M$

—($CH_2$—CH)—
|
$O(CH_2CH_2O)_{15}(CH_2)_{15}OPhPhCOO^-M$

—($CH_2$—CH)—
|
$O(CH_2CH_2O)_2(CH_2)_{20}OPhPhCOO^-M$

—($CH_2$—CH)—
|
$O(CH_2)_8O(CH_2)_2OPhPhCOO^-M$

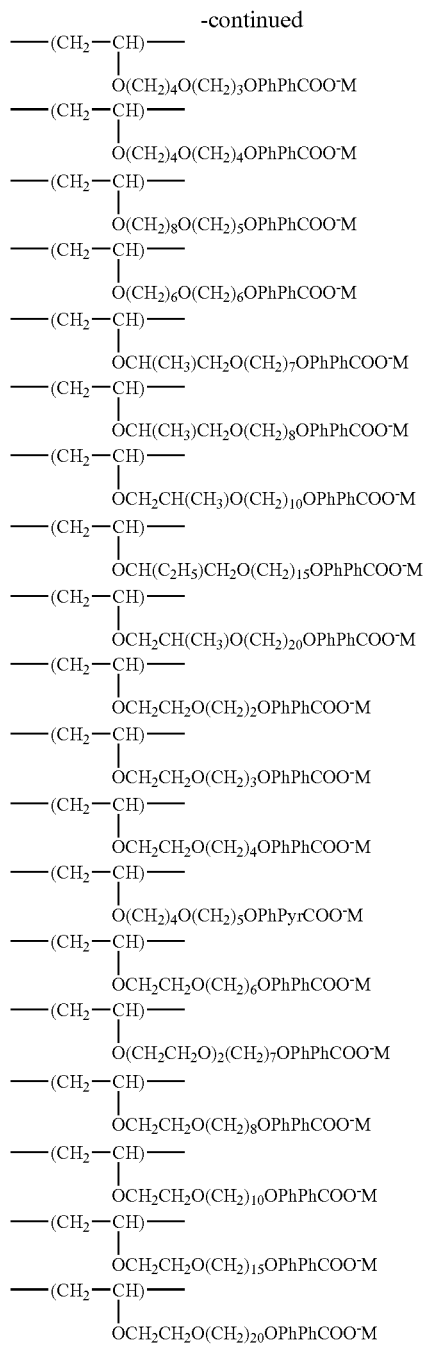

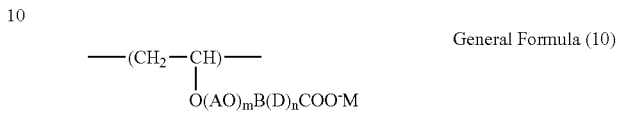

wherein Ph is 1,4-phenylene or 1,3-phenylene; Py is 2,5-pirimidylene; 2,5-Pyr is pyridylene; and Np is 2,6-naphthylene, 1,4-naphthylene or 1,5-naphthylene.

Preferably, in the general formula (5), A is an alkylene group of a carbon number of 2 to 10, where A may be substituted with methyl, ethyl, propyl, phenyl or the like; m is an integer of 1 to 10;

B is an alkylene group being methylene, ethylene, propylene, butylenes, pentylene, hexylene, heptylene, octylene or the like;

D is phenylene, pyridylene, pirimidylene, naphthylene, anthranylene, phenanthranylene, thiophenylene, furanylene or the like;

n is an integer of 2 to 5;

M is a monovalent metal cations, e.g., sodium, potassium and lithium or a polyvalent metal cation such as magnesium, calcium, nickel and iron. When M is a polyvalent metal cation, it forms an ion pair with 2 or more COO⁻ anions.

The repeating monomer unit represented by the general formula (5) is preferably the one represented by the general formula (10):

$$\text{—(CH}_2\text{—CH)—} \atop \text{O(AO)}_m\text{B(D)}_n\text{COO}^-\text{M} \qquad \text{General Formula (10)}$$

wherein A is ethylene or propylene; m is an integer of 0 to 5, and when m is 2 or more, A may be different at each occurrence; B is a single bond or alkylene of 1 to 5 carbon atoms; D is phenylene or naphthylene; n is an integer of 2 to 5, and when n is 2 or more, D may be different at each occurrence; and M is a mono- or polyvalent metal cation.

The polymer compound comprising the monomer units represented by the general formula (5) can be produced by alkaline hydrolysis of the terminal ester segment of a polymer compound comprised of the corresponding monomer unit represented by the general formula (4). It may be also produced by acid hydrolysis followed by alkali treatment. However, the former process is more preferable.

The polymer compound comprising monomer units represented by the general formula (5) has a number-average molecular weight of 200 to 10,000,000, preferably 1000 to 1,000,000. Those having a molecular weight above 10,000,000 may not be readily dispersed in a solvent, because of excessive entanglement within or between the polymer chains, and those of a molecular weight below 200 may not exhibit full steric effect of a polymer compound due to too small molecular weight. The polymer compound of the present invention may be a homopolymer comprising a single monomer unit or copolymer comprising two or more monomer units. In the case of copolymer, it contains a monomer unit represented by the general formula (5) preferably at 1% by mole or more, more preferably 3% by mole or more. When the content of the monomer unit represented by the general formula (5) is lower than 1% by mole, functions such as dispersion improvement may not be satisfactorily exhibited. Preferably, the copolymer contains vinyl ether monomer units 50% by mole or more of the monomer units, more preferably 80% by mole or more.

The polymer compound of each of the fifth and sixth aspects of the present invention is suitably used as a component for a composition of the first aspect of the present invention.

<Polymer Compound of the Seventh Aspect>

The seventh aspect of the present invention is the block polymer compound having a monomer unit represented by the general formula (1).

In the general formula (1) representing the monomer unit contained in the block polymer compound of the present invention, carbon number of A, the preferable ranges of m and n, and specific examples of A, B, D and R are the same as those in the general formula (1) for the polymer compound of the first aspect.

More specifically, in the general formula (1), A as an alkylene group preferably has a carbon number of 2 to 10. The alkylene group as A may be substituted with methyl, ethyl, propyl, phenyl or the like.

m is an integer preferably of 1 to 10.

B as an alkylene group is methylene, ethylene, propylene, butylenes, pentylene, hexylene, heptylene, octylene or the like.

D as an aromatic ring structure is phenylene, pyridylene, pirimidylene, naphthylene, anthranylene, phenanthranylene, thiophenylene, furanylene or the like.

n is an integer preferably of 1 to 5.

R as an alkyl group preferably has a carbon number of 1 to 10. R as an aromatic ring structure is phenyl, pyridyl, biphenyl group or the like. It may be substituted with an alkyl, alkoxy group, or the like.

The preferable monomer unit represented by the general formula (6) is the preferable one included in the block polymer of the present invention.

The specific examples of the repeating monomer unit represented by the general formula (1) are also the specific ones for the block polymer compound of the present invention.

The block polymer compound can be produced preferably by polymerization of the polymerizable compound represented by the general formula (3). This process is mainly effected by cationic polymerization in the presence of a polymerization initiator. The polymerization initiators useful for the above process include protonic acids, e.g., hydrochloric, sulfuric, methanesulfonic, trifluoroacetic, trifluoromethanesulfonic and perchloric acid; and combinations of Lewis acid (e.g., $BF_3$, $AlCl_3$, $TiCl_4$, $SnCl_4$, $FeCl_3$, $RAlCl_2$ or $R_{1.5}AlCl_{1.5}$, where R is an alkyl) and cation source (e.g., protonic acid and water, alcohol or adduct of vinyl ether and carboxylic acid). The polymer compound can be produced by the polymerization of the polymerizable compound (monomer) represented by the general formula (3) proceeding in the presence of the polymerization initiator.

Next, the polymerization process more suitably used for the present invention is described. A number of processes have been proposed for production of polymers comprised of polyvinyl ether monomer units (e.g., Patent Document 10). Representative one is cation living polymerization proposed by Aoshima et al (Patent Documents 11 and 12). Cation living polymerization can produce various polymers with a precise length (molecular weight), and these polymers include homopolymers, copolymers comprised of plural monomer components, block polymers, graft polymers and graduation polymers. Alternatively, living polymerization process can be carried out using $HI/I_2$ or $HCl/SnCl_4$.

The block polymer compound of the seventh aspect has a block segment comprised of monomer units represented by the general formula (1), and at least one block segment different from the above segment.

The monomer unit constituting the block segment different from that represented by the general formula (1) is preferably represented by the general formula (11):

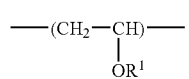

General Formula (11)

wherein $R^1$ is selected from the group consisting of a straight, branched or cyclic alkyl group of 1, to 18 carbon atoms, Ph, Pyr, Ph-Ph, Ph-Pyr, —$(CH(R^2)$—$CH(R^3)$—$O)_p$—$R^4$ and —$(CH_2)m$—$(O)_n$—$R^4$, where the aromatic ring may be substituted with a straight or branched alkyl group of 1 to 4 carbon atoms, and carbon atom in the aromatic ring may be replaced by nitrogen atom;

p is an integer of 1 to 18, m is an integer of 1 to 36, and n is 0 or 1;

$R^2$ and $R^3$ are each independently a hydrogen atom or $CH_3$;

$R^4$ is selected from the group consisting of hydrogen atom, a straight, branched or cyclic alkyl group of 1 to 18 carbon atoms, Ph, Pyr, Ph-Ph, Ph-Pyr, —CHO, —CO—CH=$CH_2$, —CO—$C(CH_3)$=$CH_2$ and —$CH_2COOR^7$, and when $R^4$ is other than hydrogen atom, the hydrogen atom bound to the carbon atom may be replaced by a straight-chain or branched alkyl group of 1 to 4 carbon atoms, or F, Cl or Br, and the carbon atom in the aromatic ring may be replaced by nitrogen atom;

$R^7$ is hydrogen atom, or an alkyl group of 1 to 4 carbon atoms; and

Ph is phenyl group, and Pyr is pyridyl group.

More specifically, these monomer units include:

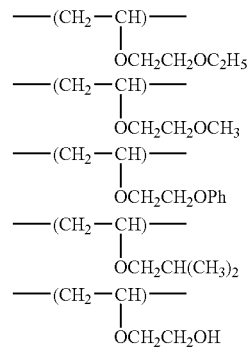

The block polymer of the present invention contains the monomer units represented by the general formula (1) 0.01 to 99.5% by mole of the polymer compound, preferably 1 to 95%. If the content is lower than 0.01%, it may have an insufficient interaction on the polymer compound, above 99.5%, it may exhibit its function insufficiently, because of the excessive interaction conversely. The monomer units other than those represented by the general formula (1) are incorporated at 0.5 to 99.99% by mole of the polymer compound, preferably 5 to 99%.

The block polymer compound comprising monomer units represented by the general formula (1) has a number-average molecular weight (Mn) of 200 to 10,000,000, preferably 1000 to 1,000,000. The compound having a molecular weight above 10,000,000 may not be readily dispersed in a solvent, because of excessive entanglement within or between the polymer chains. On the other hand, those having a molecular weight below 200 may be difficult to fully exhibit the steric effect as a polymer compound, because of excessively low molecular weight.

<Block Polymer Compound of the Eighth Aspect>

The eighth aspect of the present invention is a block polymer compound comprised of monomer units represented by the general formula (2).

In the general formula (2) representing the monomer unit contained in the block polymer compound of the present invention, the preferable A, m, B, D, n, M, and their specific examples are the same as described for the second aspect above.

Specific examples of the monomer units represented by the general formula (2) in the second aspect of the present inventions are also those of the monomer units for the block polymer of the present invention.

The block polymer compound having a monomer unit represented by the general formula (2) can be produced by alkali hydrolysis of the terminal ester segment of a polymer compound comprised of corresponding monomer units represented by the general formula (1). It may be also produced by acid hydrolysis, followed by alkali treatment. However, the former process is more preferable. It may be also produced by hydrolysis in the presence of an alkali, followed by cation exchanging.

The polymer compound of the eighth aspect has a block segment, and at least one block segment having a structure different from that of the former. The monomer units constituting the block segment different from that represented by the general formula (2) is preferably represented by the general formula (11).

The monomer unit represented by the general formula (2) to be contained in the block polymer compound of the present invention is incorporated at 0.01 to 99.5% by mole of the whole polymer compound, preferably 1 to 95%. Its content beyond the above range is not desirable; it may have an insufficient interaction on the polymer compound when present at below 0.01%, and may exhibit its function insufficiently when present at above 99.5% because of the excessive interaction conversely. The monomer unit other than that represented by the general formula (2) is incorporated at 0.5 to 99.99% by mole of the whole polymer compound, preferably 5 to 99%.

The block polymer compound comprising monomer units represented by the general formula (2) has a number-average molecular weight (Mn) of 200 to 10,000,000, preferably 1000 to 1,000,000. The compound having a molecular weight above 10,000,000 may not be readily dispersed in a solvent, because of excessive entanglement within or between the polymer chains. On the other hand, those having a molecular weight below 200 may be difficult to fully exhibit the steric effect as a polymer compound, because of excessively low molecular weight.

One of the favorable properties which the block polymer compounds of the seventh and eighth aspects are expected to exhibit is an amphipathic property. This property can be realized by providing the compound with hydrophobic and hydrophilic block segments simultaneously. The block polymer compound of the present invention can form a micellar condition in an aqueous solvent, when it is amphipathic. In such a case, the amphipathic polymer compound has properties desirable properties for recording materials, which is discussed later.

For improved dispersion stability and inclusion capacity, it is preferable for the block polymer to have more flexible molecular motion in view of entanglement and affinity with the functional material. Flexible block polymers are also preferable because it can easily form a coating layer on a recording medium, as discussed later. For this reason, glass transition temperature Tg of the main chain of the block polymer is preferably 20° C. or lower, more preferably 0° C. or lower, still more preferably −20° C. or lower. Generally speaking, polyvinyl ether polymers have a low Tg and flexibility. Most of the above monomer units have a glass transition temperature of around −20° C. or lower.

The polymer compounds of the fifth and sixth aspects of the present invention, and block polymer compounds of the seventh and eighth aspects are each the preferable component for the composition of the first aspect of the present invention.

Each segment in the block polymer compound may be composed of a single monomer unit, or 2 or more monomer units. Moreover, the block polymer compound of the present invention may be a di-, tri- or tetra-block polymer or higher. It may be also a block polymer graft-bonded to another polymer.

<Block Polymer Compound of the Ninth Aspect>

The block polymer compound of the present invention is characterized by having an aromatic carboxylic acid structure. One of the characteristics of an aromatic carboxylic acid is a high acidity in comparison with carbolic acid, or aliphatic carboxylic acids, that is, it has a lower pKa representing acidity. This means that dissociation degree of aromatic carboxylic acid or its alkali salt is high. As such, it can realize a block polymer having high amphipathic properties, which can disperse functional material and stabilize the dispersion efficiently.

The block polymer of the present invention can be an organic acid and its alkali salt having a pKa value of 4.5 or less, more preferably 4.3 or less. Thus, due to its high dissociation degree, it realizes a block polymer having high amphipathic properties, as well as higher dispersibility and dispersion stability of a functional material. pKa value is a dissociation index of an acid. pKa can be determined from its concentration and hydrogen ion concentration in water as described below.

In the present invention, when pKa of a polymer is determined, the concentration is mole concentration of the monomer units having acidic functional group, not the mole concentration of the polymer. The mole concentration of the monomer units can be determined by acid-base titration, or by NMR analysis.

In a dilute aqueous solution, acid dissociation constant Ka is represented by $[H_3O^+][B^-]/[BH]$, where BH is an organic acid, $B^-$ is the conjugate base of the organic acid. pKa is −logKa.

pKa can be determined by using hydrogen ion concentration measured by a pH meter and the above-defined mole concentration.

As described above, the present invention provides a polymer compound which is suitably used to prepare an ink or a toner composition by dispersing a colorant or solid component more efficiently. The composition of the present invention is suitably used for various image-forming methods, e.g., electrophotography and ink-jet printing.

Moreover, the polymer compound of the present invention, with a solvent or dispersion medium, can provide compositions of the present invention, e.g., ink or toner compositions, and recording materials.

The present invention is described in more detail by EXAMPLES, which by no means limit the present invention.

EXAMPLE 1

Synthesis of

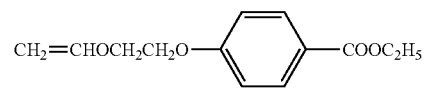

A mixture of 0.8 mols of potassium carbonate, 0.42 mols of ethyl 4-hydroxybenzoate and 4 g of tetrabutyl ammonium iodide in 300 mL ethanol and 0.42 mols of 2-chloroethyl vinyl ether was heated under reflux for 40 hours in a nitrogen atmosphere. The reaction mixture was filtered, distilled to remove the solvent, then applied to column chromatography, and recrystallized from methanol. This produced

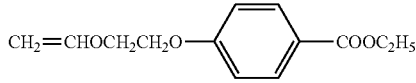

99.9% pure as determined by gas chromatography, in a yield of 32%.

The compound prepared in EXAMPLE 1 was hydrolyzed, and the resultant carboxylic acid had a pKa value of 4.38 in water.

EXAMPLE 2

Synthesis of Polymer Compound (1)

0.1 mols of the polymerizable compound prepared in EXAMPLE 1, 0.001 mols of water and 0.005 mols of ethyl aluminum dichloride were reacted by cationic polymerization in anhydrous toluene.

The reaction was allowed to proceed for 20 hours, and then stopped adding methylene chloride and water to the reaction mixture. The mixture was washed with water, with dilute hydrochloric acid and then with an alkali, dried on anhydrous sodium sulfate, and distilled to remove the solvent, to produce a high molecular weight compound (polymer). It had a number-average molecular weight of 4,100, determined by volume exclusion chromatography.

EXAMPLE 3

Synthesis of

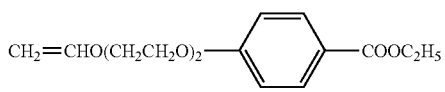

was prepared in the same manner as in EXAMPLE 1, except that ethyl 4-hydroxybenzoate was replaced by CH$_2$=CHOCH$_2$CH$_2$OCH$_2$CH$_2$OTs (Ts is tosyl group) (yield: 21%).

EXAMPLE 4

Synthesis of

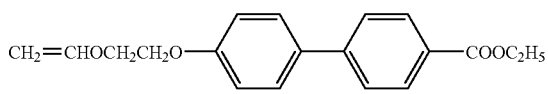

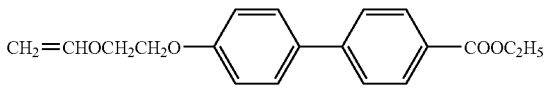

COOC$_2$H$_5$ was prepared in the same manner as in EXAMPLE 1, except that ethyl 4-hydroxybenzoate was replaced by ethyl 4-(4'-hydroxyphenyl)benzoate (yield: 22%).

The polymerizable compound prepared in each of EXAMPLES 3 and 4 was polymerized in a manner similar to that for EXAMPLE 2, to prepare the polymer compound. These compounds had number-average molecular weights of 1,800 and 3,400, respectively, determined by volume exclusion chromatography.

EXAMPLE 5

Synthesis of Polymer Compound (2)

The polymer compound prepared in EXAMPLE 2 was stirred with a 5N aqueous solution of sodium hydroxide at room temperature (23° C.) for 40 hours to hydrolyze the ester. The reaction mixture was neutralized with 5N hydrochloric acid, extracted with methylene chloride, dried, distilled to remove the solvent so as to obtain free carboxylic acid polymer. Neutralized with the same amount of 1N sodium hydroxide and distilled to remove water, sodium carboxyl ate salt polymer was obtained.

EXAMPLE 6

Production of Ink Composition (1)

Three parts of pigment (Cabot's Mogul L), 5 parts of the polymer compound prepared in EXAMPLE 2 and 15 parts of diethylene glycol were dispersed in 77 parts of ion-exchanged water by an ultrasonic homogenizer, all parts by weight. The resulting dispersion was filtered through a 1 μm filter under pressure, to prepare an ink composition. The pigment was found well dispersed.

EXAMPLE 7

Production of Ink Composition (2)

Three parts of pigment (Cabot's Mogul L), 5 parts of the sodium carboxylate salt type polymer prepared in EXAMPLE 5 and 15 parts of diethylene glycol were dispersed in 79 parts of ion-exchanged water using an ultrasonic homogenizer, all parts by weight. The resulting dispersion was filtered through a filter of 1 μm pore size under pressure, to prepare an ink composition. The pigment was found well dispersed.

EXAMPLE 8

Printing Test (1)

The ink-jet printing test was carried out using the ink composition prepared in EXAMPLE 7. Normal paper was printed with this ink composition by an ink jet printer (Canon's Bubble Jet Printer BJF800). The fine, black letters were printed.

EXAMPLE 9

Production of Toner Composition (1)

The free carboxylic acid polymer as the precursor for the sodium carboxylate polymer prepared in EXAMPLE 5 was used to prepare a toner composition by the following procedure.

100 parts of a polyester resin (synthesized from bisphenol A, terephthalic acid, n-dedecenylsuccinic acid, trimellitic acid and diethylene glycol in a molar ratio of 20:38:10:5:27), 70 parts of magnetite ($Fe_3O_4$), 3 parts of the free carboxylic acid polymer described above, 2 parts of triphenylmethane-based dye and 3 parts of a low-molecular weight polypropylene, all parts by weight, were preliminarily mixed, and then molten/kneaded by an extruder. The mixture was cooled, roughly divided by a speed mill, finely divided by a jet mill and classified by a zigzag classifier, to produce a toner having a volume-average diameter of 11 μm.

100 parts of the toner was mixed with 0.4 parts of positively chargeable, hydrophobic, dry type silica, treated with an amino-modified silicone oil (viscosity: 100 cp at 25° C. and amine equivalents: 800) and 0.2 parts of spherical PVDF particles (average particle diameter: 0.2 μm) by a Henschel mixer, all parts by weight, to prepare a positively chargeable toner composition. The toner composition gave a fine copy on a copier (Canon's copier NP-3525).

<Synthesis of Block Polymer Compound and Production of Composition>

In EXAMPLES 10 to 18, the polymerizable compound prepared in EXAMPLE 1 is referred to as Monomer B.

EXAMPLE 10

Synthesis of AB Block Polymer Compound of Isobutyl Vinyl Ether (IBVE: Block Component A) and Monomer B (Block Component B)

A glass container equipped with a stop cock was purged with nitrogen, and heated at 250° C. to remove adsorbed water. The container was cooled to room temperature, and charged with 12 mmols of IBVE, 16 mmols of ethyl acetate, 0.05 mmols of 1-isobutoxyethyl acetate and 11 mL of toluene. The reaction was cooled, to which 0.2 mmols of ethyl aluminum sesqui-chloride (equimolar mixture of diethyl aluminum chloride and ethyl aluminum dichloride) was added at 0° C. to initiate the polymerization to synthesize the component A for the AB block polymer. Molecular weight of the component A (IBVE) was monitored periodically by molecular-sieve column chromatography (GPC) to determine completion of the polymerization.

Then a toluene solution containing 10 mmols of Monomer B (block component B) was added to the reaction, and the polymerization was continued for 20 hours and then stopped by adding an aqueous solution of 0.3% by weight of ammonia/methanol. The reaction mixture was diluted with dichloromethane, and washed 3 times with 0.6M hydrochloric acid and then 3 times with distilled water. The resulting organic phase was concentrated to dryness on an evaporator, dried under a vacuum, and dialyzed repeatedly through a semi-permeable membrane of cellulose in a methanol solvent to remove the monomer compound, to prepare a diblock polymer as the target product. The polymerization ratio A/B was 100/28. The compound was identified by NMR and GPC. It had an Mn value of 30,700 and Mw/Mn ratio of 1.38.

EXAMPLE 11

The block polymer compound prepared in EXAMPLE 10 was hydrolyzed in a mixed aqueous solution of dimethylformamide and sodium hydroxide. As a result, side chains of the block component B were hydrolyzed, yielding a diblock polymer sodium salt. The compound was identified by NMR and GPC.

It was further neutralized with 0.1N hydrochloric acid in a water dispersion to have the component B converted into free carboxyl group. The compound was identified by NMR and GPC.

The carboxylic acid segment in the above block polymer had a pKa value of 4.29 in water.

EXAMPLE 12

Synthesis of Block Polymer (2)

A block polymer was prepared in the same manner as in EXAMPLE 10, except that IBVE as the component B for the block polymer was replaced by 2-ethoxyethyl vinyl ether. Its polymerization ratio A/B was 100/29. It had an Mn value of 28,700 and Mw/Mn ratio of 1.45.

EXAMPLE 13

Production of Ink Composition (3)

3 parts of a black-color pigment (Cabot's Mogul L), 4 parts of the sodium salt type block polymer prepared in EXAMPLE 11 and 15 parts of diethylene glycol were dispersed in 78 parts of ion-exchanged water by an ultrasonic homogenizer, all parts by weight. The resulting dispersion was filtered through a 1 μm filter under pressure, to prepare an ink composition. The pigment was found well dispersed.

EXAMPLE 14

Print Test (2)

The ink-jet printing test was carried out using the ink composition prepared in EXAMPLE 13, where a common paper was printed with the ink composition prepared in EXAMPLE 13 by an ink jet printer (Canon's Bubble Jet Printer BJF800), whose ink tank was filled with the composition. The fine, black letters were printed.

EXAMPLE 15

Production of Toner Composition (2)

The diblock polymer of free carboxylic acid form prepared in EXAMPLE 11 was used to prepare a toner composition by the following procedure.

100 parts of a polyester resin (synthesized from bisphenol A, terephthalic acid, n-dedecenylsuccinic acid, trimellitic acid and diethylene glycol in a molar ratio of 20:38:10:5:27), 70 parts of magnetite ($Fe_3O_4$), 3 parts of the free carboxylic acid polymer prepared in EXAMPLE 11, 2 parts of triphenylmethane dye and 3 parts of a low-molecular weight polypropylene, all parts by weight, were preliminarily mixed, and then molten/kneaded by an extruder. The mixture was cooled, roughly divided by a speed mill, finely pulverized by a jet mill and classified by a zigzag classifier, to produce a toner having a volume-average diameter of 11 μm.

100 parts of the toner was mixed with 0.4 parts of positively chargeable, hydrophobic, dry type silica that had been treated with an amino-modified silicone oil (viscosity: 100 cp at 25° C. and amine equivalents: 800) and 0.2 parts of spherical PVDF particles (average particle diameter: 0.2 μm) by a Henschel mixer, all parts by weight, to prepare a positively-chargeable toner composition. The toner composition gave a fine, black-colored copy using a copier (Canon's product NP-3525).

EXAMPLE 16

Production of Ink Composition (4)

26 parts of the diblock polymer of free carboxylic form prepared in EXAMPLE 11 and 10 parts of an oil-soluble dye (Oil Blue N, Aldrich) were co-dissolved in dimethylformamide, and the solution was turned into an aqueous phase with 400 parts of distilled water, all parts by weight, to prepare an ink composition. The Oil Blue component was not separated or precipitated, when the ink composition was left to stand for 10 days.

The diblock polymer prepared in EXAMPLE 12 was hydrolyzed in a manner similar to that in EXAMPLE 11 to prepare a block polymer of carboxylic acid salt form. 26 parts of the block polymer and 10 parts of an oil-soluble dye (Aldrich's Oil Blue N) were co-dissolved in dimethylformamide, and the solution was turned into an aqueous phase with 400 parts of distilled water, all parts by weight, to prepare an ink composition in the same manner as in EXAMPLE 16. It is known that the poly-2-ethoxyethyl vinyl ether segment being the hydrophobic segment of the compound becomes hydrophilic at low temperature. When the compound was cooled to 0° C., the oil-soluble dye (Oil Blue) separated out, indicating that the dye had been included in the polymer micelles.

EXAMPLE 17

Thickening

The dispersion of micelles holding the oil-soluble dye, prepared in EXAMPLE 16, was treated with 2N hydrochloric acid to be pH 3. As a result, the composition became greatly viscous to have a viscosity of 0.250 Pas (250 cps). When the same printing test was carried out as in EXAMPLE 8 on normal paper sprayed with hydrochloric acid, fine prints were obtained. When these prints were rubbed with a line marker, no blue tailing was observed, proving good fixability and water resistance of the print.

EXAMPLE 18

A diblock polymer compound was prepared in the same manner as in EXAMPLE 10, except that Monomer B was replaced by a monomer having a structure represented by

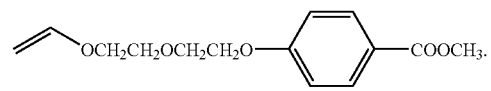

A composition was prepared in the same manner as in EXAMPLE 13 using the above polymer, and print test by ink-jet system was carried out also in the same manner as in EXAMPLE 8. The fine prints were obtained.

Comparative Example

An ink composition was prepared using styrene-sodium acrylate copolymer (polymerization ratio: 100/30, number-average molecular weight: 33,000) in the same manner as in EXAMPLE 13. The printing test was also carried out in the same manner as in EXAMPLE 8 using a BJF800 printer, whose ink tank was filled with the composition. It could not be discharged from the printer, and no print was obtained.

What is claimed is:

1. A polymer compound comprising a monomer unit represented by the general formula (5):

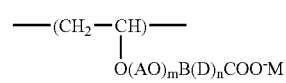

wherein A is a straight-chain or branched alkylene group of 1 to 15 carbon atoms with or without substitution; m is an integer of 0 to 30, and when m is 2 or more, A is the same or different from each other; B is a single bond or alkylene with or without substitution; D is an aromatic ring structure; n is an integer of 2 to 10, and D is the same or different from each other; and M is a mono- or poly-valent metal cation.

2. A block polymer compound having a block segment comprising a monomer unit represented by the general formula (1):

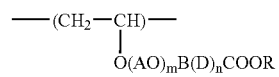

wherein A is a straight-chain or branched alkylene group of 1 to 15 carbon atoms with or without substitution; m is an integer of 0 to 30, and when m is 2 or more, A is the same or different from each other; B is a single bond or alkylene with or without substitution; D is an aromatic ring structure; n is an integer of 1 to 10, and when n is 2 or more, D is the same or different from each other; and R is a hydrogen atom, an alkyl group with or without substitution, an aromatic ring structure without substitution, or an aromatic ring structure substituted with an alkyl group, and wherein the block polymer has at least one block segment different than that represented by general formula (1), is amphipathic and includes hydrophobic and hydrophilic block segments.

3. A block polymer compound having a block segment comprising a monomer unit represented by the general formula (2):

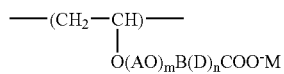

wherein A is a straight-chain or branched alkylene group of 1 to 15 carbon atoms with or without substitution; m is an integer of 0 to 30, and when m is 2 or more, A is the same or different from each other; B is a single bond or alkylene with or without substitution; D is an aromatic ring structure; n is an integer of 1 to 10, and when n is 2 or more, D is the same or different from each other; and M is a mono- or poly-valent metal cation and wherein the block polymer has at least one block segment different than that represented by general formula (2).

4. The block polymer compound according to claim 3, wherein the block polymer is amphipathic.

* * * * *